(12) United States Patent
Wood et al.

(10) Patent No.: US 8,938,288 B2
(45) Date of Patent: *Jan. 20, 2015

(54) METHODS AND DEVICES FOR RELIEVING STRESS

(75) Inventors: Michael Wood, Miami Beach, FL (US);
Adam Forbes, New York, NY (US);
Kirstin Rhys, Brooklyn, NY (US)

(73) Assignee: Respironics, Inc., Murrysville, PA (US)

( * ) Notice: Subject to any disclaimer, the term of this patent is extended or adjusted under 35 U.S.C. 154(b) by 1330 days.

This patent is subject to a terminal disclaimer.

(21) Appl. No.: 12/708,643

(22) Filed: Feb. 19, 2010

(65) Prior Publication Data

US 2010/0174200 A1 Jul. 8, 2010

Related U.S. Application Data

(63) Continuation of application No. 11/084,456, filed on Mar. 18, 2005, now Pat. No. 7,691,049.

(60) Provisional application No. 60/554,211, filed on Mar. 18, 2004.

(51) Int. Cl.
*A61B 5/0205* (2006.01)
*A61B 5/00* (2006.01)
*A61B 5/024* (2006.01)
*G09B 23/28* (2006.01)
*A61B 5/08* (2006.01)

(52) U.S. Cl.
CPC ........... *A61B 5/0059* (2013.01); *A61B 5/02405* (2013.01); *A61B 5/486* (2013.01); *G09B 23/288* (2013.01); *A61B 5/02416* (2013.01); *A61B 5/0816* (2013.01)

USPC .......................................... 600/515; 600/484

(58) Field of Classification Search
USPC .................................... 600/515, 509, 484, 26
See application file for complete search history.

(56) References Cited

U.S. PATENT DOCUMENTS

| | | |
|---|---|---|
| 4,510,944 A | 4/1985 | Porges |
| 4,519,395 A | 5/1985 | Hrushesky |
| 4,960,129 A | 10/1990 | De Paola et al. |
| 5,148,812 A | 9/1992 | Verrier et al. |
| 5,265,617 A | 11/1993 | Verrier et al. |
| 5,277,189 A | 1/1994 | Jacobs |
| 5,291,400 A | 3/1994 | Gilham |
| 5,423,325 A | 6/1995 | Burton |
| 5,520,192 A | 5/1996 | Kitney et al. |
| 5,579,775 A | 12/1996 | Dempsey et al. |
| 5,603,331 A | 2/1997 | Heemels et al. |
| 5,682,901 A | 11/1997 | Kakmen |
| 5,687,734 A | 11/1997 | Dempsey et al. |
| 5,718,235 A | 2/1998 | Golosarsky et al. |
| 5,807,247 A | 9/1998 | Merchant et al. |
| 5,853,364 A | 12/1998 | Baker, Jr. et al. |
| 5,891,044 A | 4/1999 | Golosarsky et al. |
| 5,997,482 A | 12/1999 | Vaschillo et al. |
| 6,002,952 A | 12/1999 | Diab et al. |
| 6,026,320 A | 2/2000 | Carlson et al. |
| 6,083,172 A | 7/2000 | Baker, Jr. et al. |

(Continued)

*Primary Examiner* — Alyssa M Alter

(57) ABSTRACT

Easy to use, cost-effective methods and devices for evaluating and treating stress and thereby disorders caused or exacerbated by stress are provided. More particularly methods and devices for identifying RSA waves during respiration which provide a subject with near real-time RSA wave information are provided. This information can be used in biofeedback settings to assist subjects in reducing levels of stress by achieving rhythmic breathing patterns.

9 Claims, 58 Drawing Sheets

(56) References Cited

U.S. PATENT DOCUMENTS

| | | |
|---|---|---|
| 6,099,481 A | 8/2000 | Daniels et al. |
| 6,106,481 A | 8/2000 | Cohen |
| 6,144,877 A | 11/2000 | De Petrillo |
| 6,179,784 B1 | 1/2001 | Daniels et al. |
| 6,212,427 B1 | 4/2001 | Hoover |
| 6,269,263 B1 | 7/2001 | Ohnishi et al. |
| 6,305,943 B1 | 10/2001 | Pougatchev et al. |
| 6,358,201 B1 | 3/2002 | Childre et al. |
| 6,411,833 B1 | 6/2002 | Baker, Jr. et al. |
| 6,416,473 B1 | 7/2002 | Risk et al. |
| 6,487,442 B1 | 11/2002 | Wood |
| 6,490,480 B1 | 12/2002 | Lerner |
| 6,529,772 B2 | 3/2003 | Carlson et al. |
| 6,532,382 B2 | 3/2003 | Meier et al. |
| 6,539,249 B1 | 3/2003 | Kadhiresan et al. |
| 6,572,558 B2 | 6/2003 | Masakov et al. |
| 6,626,843 B2 | 9/2003 | Hillsman |
| 6,656,116 B2 | 12/2003 | Kim et al. |
| 6,658,276 B2 | 12/2003 | Kianl et al. |
| 6,678,547 B2 | 1/2004 | Carlson et al. |
| 6,699,194 B1 | 3/2004 | Diab et al. |
| 6,702,752 B2 | 3/2004 | Dekker |
| 6,731,974 B2 | 5/2004 | Levitan et al. |
| 6,805,673 B2 | 10/2004 | Dekker |
| 6,836,681 B2 | 12/2004 | Stabler et al. |
| 6,850,788 B2 | 2/2005 | Al-Ali |
| 2002/0045806 A1 | 4/2002 | Baker, Jr. et al. |
| 2002/0111555 A1 | 8/2002 | Stabler et al. |
| 2002/0137994 A1 | 9/2002 | Baker, Jr. et al. |
| 2002/0161291 A1 | 10/2002 | Kianl et al. |
| 2003/0018357 A1 | 1/2003 | Luthra et al. |
| 2003/0045807 A1 | 3/2003 | Daniels et al. |
| 2003/0078505 A1 | 4/2003 | Kim et al. |
| 2003/0163034 A1 | 8/2003 | Dekker |
| 2003/0163050 A1 | 8/2003 | Dekker |
| 2003/0163054 A1 * | 8/2003 | Dekker .................. 600/502 |
| 2003/0181798 A1 | 9/2003 | Al-Ali |
| 2004/0019289 A1 | 1/2004 | Ross |
| 2004/0122486 A1 | 6/2004 | Stahmann et al. |
| 2004/0122487 A1 | 6/2004 | Hatlestad et al. |
| 2004/0127804 A1 | 7/2004 | Hatlesad et al. |
| 2004/0181134 A1 | 9/2004 | Baker, Jr. |
| 2004/0230104 A1 | 11/2004 | Yangidaira et al. |
| 2004/0230252 A1 | 11/2004 | Kullok et al. |
| 2004/0236236 A1 | 11/2004 | Yanagidaira et al. |
| 2004/0249299 A1 | 12/2004 | Cobb |
| 2004/0260186 A1 | 12/2004 | Dekker |
| 2005/0021092 A1 | 1/2005 | Yun et al. |
| 2005/0033189 A1 | 2/2005 | Mc Craty et al. |

* cited by examiner $p\text{-}p_0 = abs\ (p_1 - p_0) = abs\ (1{,}010\ ms - 10\ ms) = 1{,}000\ ms$ $p\text{-}p_1 = abs\ (p_2 - p_1) = abs\ (1{,}860\ ms - 1{,}010\ ms) = 850\ ms$ $p\text{-}p_2 = abs\ (p_3 - p_2) = abs\ (2{,}560 - 1{,}860) = 700\ ms$ $p\text{-}p_0 = abs\ (p_1 - p_0) = abs\ (1{,}010\ ms\ -10\ ms) = 1{,}000\ ms$ $p\text{-}p_1 = abs\ (p_2 - p_1) = abs\ (1{,}860\ ms\ -1{,}010\ ms) = 850\ ms$ $p\text{-}p_2 = abs\ (p_3 - p_2) = abs\ (2{,}560\ ms\ -1{,}860\ ms) = 700\ ms$ $IBI_0 = abs\ (pp_0 - pp_1) = abs\ (1{,}000\ ms\ -850\ ms) = 150\ ms$ $IBI_1 = abs\ (pp_1 - p\text{-}p_2) = abs\ (850\ ms\ -700\ ms) = 150\ ms$ $PP_b$ is a top point (tp)

$pp_a$ = 600 ms
$pp_b$ = 750 ms
$pp_c$ = 610 ms $PP_b$ is a bottom point (bp)

$pp_a$ = 700 ms
$pp_b$ = 550 ms
$pp_c$ = 600 ms $PP_b$ is an ascending transition point (ap)

$pp_a$ = 600 ms
$pp_b$ = 650 ms
$pp_c$ = 700 ms $PP_b$ is a descending transition point $pp_a$ = 600 ms
$pp_b$ = 550 ms
$pp_c$ = 500 ms $Wave_1 = (P_0 \text{ (left valley)} \quad P_6 \text{ (peak)} \quad P_8 \text{ (right valley)}$ $Wave_2 = (P_8 \text{ (left valley)} \quad P_{10} \text{ (peak)} \quad P_{12} \text{ (right valley)}$ $Wave_3 = (P_{12} \text{ (left valley)} \quad P_{13} \text{ (peak)} \quad P_{15} \text{ (right valley)}$ 10 seconds = 6 waves/minute
Rhythmic breathing at six breaths per minute

| Summary | |
|---|---|
| Total Time | 5:00 |
| Relaxation Points | 24 |

FIG. 29

Can't see the
waves because
error consumes
the screen

METHODS AND DEVICES FOR RELIEVING STRESS

RELATED APPLICATION

This is continuation of U.S. Ser. No. 11/084,456 filed Mar. 18, 2005 and is incorporated by reference herein.

This application claims priority to and benefit from U.S. Provisional Application No. 60/554,211, filed Mar. 18, 2004 and is incorporated herein.

FIELD OF INVENTION

The present invention relates to methods and devices for evaluating and treating stress and stress-related disorders. More particularly the present invention relates to biofeedback devices and methods for increasing parasympathetic nerve activity by providing information on respiratory sinus arrhythmia patterns.

BACKGROUND INFORMATION

Despite the existence of many stress reduction products and services, stress and stress-related disorders still result in staggering economic and non-economic costs. It has been estimated that in the United States alone, job stress accounts for nearly $300 billion annually in terms of productivity, absenteeism and turnover. Over and above the direct work-related costs, attempts at treating stress and stress related disorders accounted for over $17 billion in anti-depression and anti-anxiety drugs in 2002. An ever upward trend in annual costs of such pharmacological treatments continues.

In addition, stress results in significant but incalculable costs due to concomitant health problems stemming directly or indirectly from underlying stress disorders. For example, studies have shown that people experiencing stress are more susceptible to viral and non-viral diseases. A common and well-known example of this is the relationship between stress and respiratory infections. Moreover, those suffering from an illness take longer to recover if suffering from stress as well.

Chronic stress can impair both the balance of the autonomic nervous system (ANS) and the efficacy of the ANS, resulting in a myriad of stress related disorders. Impairment of the ANS results in degenerative disease and premature death. For example, a clinical study examined a single two minute measurement of the ANS from 14,025 healthy men and women between the ages of 45 and 64. After eight years, those with a lower measurement had a much greater incidence of disease and death. Three other studies (US, Denmark, and Finland) have also examined ANS function as it relates to "all cause mortality". In each study, low ANS function preceded and predicted illness and death. Literally hundreds of other studies have examined ANS function as it relates to individual illnesses such as heart disease, diabetes, and stroke. For example, the British government commissioned a study on the ANS function and heart disease. Those with the lowest ANS function had more than a 1,000% increase in mortality rate from heart attacks. Non-economic costs of stress are also significant and include the harmful effects on relationships with family, friends, neighbors and co-workers.

The human body's reaction to stress, called the "stress response," involves two basic systems: the autonomic nervous system and the endocrine system. The ANS generally innervates smooth muscles of internal organs and consists of sympathetic and parasympathetic divisions. In simple terms, the sympathetic division is responsible for mobilizing energy to respond to emergencies ("fight or flight"), express emotions or perform strenuous activities, while the parasympathetic division acts to exert a calming influence and thereby balance the sympathetic system.

The endocrine system is also involved in stress-related processes. In particular, the hypothalamic-pituitary adrenal (HPA) axis plays a major role in the endocrine system's stress response. The hypothalamus secretes peptide hormones to stimulate the pituitary glands which in turn secrete its own hormones to stimulate other endocrine glands. The adrenal glands secrete cortisol which regulates metabolism and the production of energy and regulates responses in the sympathetic and parasympathetic branches of the autonomic nervous system. Cortisol levels are directly related to the degree of an individual's stress response.

In the early 1970's Dr. Herbert Benson documented the existence of a neurological and physiological state opposite of the "stress response." This state, called the "relaxation response," has been verified by other clinical investigators. From an autonomic nervous system perspective, the stress response is characterized by high activity of the sympathetic branch while the relaxation response is characterized by high activity of the parasympathetic branch. Inducing the relaxation response by definition interrupts an activated stress response. Therefore, frequent activation of the relaxation response can prevent stressors from creating on-going (i.e., chronic) stress. Also, frequent activation of the relaxation response has been shown to reverse much of the damage, including hypertension, caused by previously encountered chronic stress.

The interaction of the two branches of the autonomic nervous system (sympathetic and parasympathetic) can be characterized by examining the small changes in the time occurring between each consecutive heart beat. When an individual is at rest, variation in the beat to beat time is caused by the parasympathetic branch. This variation will increase and decrease according to an individual's respiratory pattern. During inspiration, the parasympathetic branch is inhibited, and the heart rate will begin to rise. During expiration, the parasympathetic branch engages and lowers the heart rate. This relationship between the changing heart rate and breathing is called respiratory sinus arrhythmia (RSA). RSA measurements are mathematical calculations of the degree to which the heart rate rises and falls. When the rise and fall are greater, then the activity of the parasympathetic nervous system is greater. In other words, greater RSA indicates greater parasympathetic activity. As stated previously, a sufficient increase in parasympathetic activity shifts the body into the relaxation response thereby interrupting any pre-existing stress response.

Many attempts have been made to activate the relaxation response to treat or control stress, including both invasive and non-invasive techniques and procedures. For example, acupuncture, prescription and non prescription pharmacological treatment, and psychotherapy have all been used in attempts to relieve or control stress. However, each of these therapies involves significant costs in money and time. Moreover, the effectiveness of these treatments is often less than complete and is sometimes nearly non-existent. Effectiveness often is difficult to evaluate and is many times only temporary. In addition, pharmacological treatments frequently have undesirable side effects and some may even have addiction risks. Also, even with all the available alternatives, stress still is responsible (either directly or indirectly) for more than 80% of doctor's visits.

Accordingly, a clear need exists for methods and devices for evaluating and treating stress, wherein such methods and devices are effective, non-invasive, simple to use and inexpensive. In addition, a clear need exists for methods and devices which do not have unwanted side effects or create addiction risks.

SUMMARY OF INVENTION

The present invention provides easy to use, cost-effective methods and devices for evaluating and treating stress and thereby disorders caused or exacerbated by stress. More particularly, the present invention provides methods and devices for identifying individual RSA waves and providing a subject with near real-time RSA wave information. This information can be used, for example, in biofeedback settings to assist subjects in reducing levels of stress and achieving rhythmic breathing.

Accordingly, one exemplary embodiment of the present invention provides portable, handheld biofeedback devices for reducing stress in human subjects.

Another exemplary embodiment of the present invention provides portable, handheld biofeedback devices which contain a photoplethysmograph ("PPG") sensor and a display screen to provide subjects with near real-time information on their RSA waves.

A further exemplary embodiment of the present invention provides a methods and devices for training subjects to reduce levels of stress by achieving a respiration frequency of close to 6 breaths per minute.

Yet another exemplary embodiment of the present invention provides methods for detecting and correcting erroneous data relating to RSA waves and devices which utilize such methods.

Another exemplary embodiment of the present invention provides methods for adjusting scaling on a display screen of portable biofeedback devices and devices which utilize such methods.

Still another embodiment of the present invention identifies respiration patterns including depth, rate and volume by analyzing RSA waves and provides a display of same.

BRIEF DESCRIPTION OF DRAWINGS

FIG. 29 illustrates an exemplary display of a session summary screen.

DETAILED DESCRIPTION

Studies have shown that controlled respiration can shift the balance of the sympathetic and parasympathetic branches. Three specific respiratory components interactively determine the amount of parasympathetic innervation. These three components include frequency, tidal volume, and expiration/inspiration ratio. In general, parasympathetic activity can be increased by reducing breath frequency, increasing tidal volume, and/or increasing the expiration/inspiration ratio. Thus, altering these three variables has the potential to increase parasympathetic activity enough to effectively elicit the relaxation response non-invasively, simply, inexpensively, and without negative side-effects.

Generally speaking, biofeedback methods and devices involve training processes which allow subjects to facilitate changes in behavior or activity in order to improve or maintain one or more physiological functions. Over time, a subject can be trained with biofeedback methods and devices to exercise greater control over these functions. In contrast to other forms of therapy in which treatment is imposed upon the subject, biofeedback methods and devices allow the subject to gradually integrate the training processes into almost automatic responses.

The present invention relates to methods and devices which can provide biofeedback information and training for subjects suffering from stress and stress-related disorders. Such biofeedback information and training may be based on an analysis of respiratory sinus arrhythmia patterns and breathing that can affect such patterns.

There are no known methods for identifying individual RSA waves during spontaneous breathing using only the RSA data set. In order to correlate RSA waves with respiration, usually heart rate and respiration rate information is collected and mapped separately. One aspect of the present invention includes the identification of the individual waves within a RSA data set. A further aspect of the present invention includes the use of such wave patterns to provide subjects with near real-time respiratory feedback information based on heart rate data. Means for decreasing or adequately controlling stress levels also can be provided based on the wave pattern analysis and respiratory feedback.

Wave Pattern Identification

Figure 1:
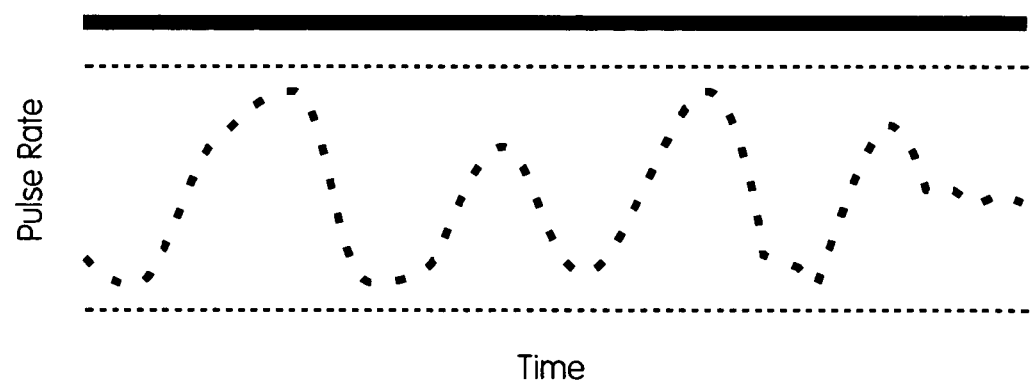
FIG. 1 illustrates a typical heart rate variability (HRV) pattern caused by respiratory sinus arrhythmia (RSA).

In one exemplary embodiment of the present invention, identification and analysis of respiratory sinus arrhythmia wave patterns begins by measuring a subject's pulse rate on a beat to beat basis. It is well established in medical literature that human heart rates, and therefore pulse rates, continually fluctuate up and down in a wave like manner (FIG. 1). These waves are known as heart rate variability (HRV) waves. When a person is physically still and resting, the HRV waves are related to a person's respiration. These resting HRV waves are medically known as respiratory sinus arrhythmia or RSA waves, as the size and shape of these waves is related to the rate, rhythm, and depth of a person's breathing. As long as a person is breathing between 4 to 15 breaths per minute, the frequency of the waves will essentially match the frequency of respiration. Most individuals breathe within this range, but even when a person is breathing outside this range, the wave frequency still provides a close approximation to the respiration frequency.

While the correlation between waves and breathing has been well established in the medical literature by visual analysis, no automated method exists to identify individual waves within a heart beat data set. An exemplary embodiment of the present invention includes a novel method of identifying each individual wave for a heart beat data set.

Figure 2:
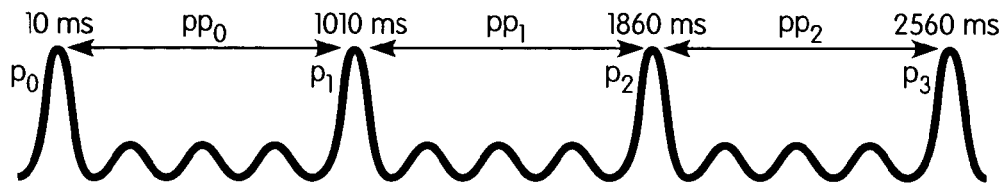
FIG. 2 illustrates an exemplary series of RSA waves and identifies several pulse peaks.

For example, the amount of time (in milliseconds) between two consecutive pulse peaks (the peak-to-peak time) is called the pp interval (pp) (FIG. 2). In an exemplary embodiment of the present invention, a device records successive pp intervals. The description of pp interval points also applies to rr intervals (the interval between consecutive R waves in an electrocardiograph or ECG), any derivative of pp intervals such as the pulse rate points, and any derivative of rr intervals such as heart rate. Collectively, these intervals may be referred to as "heart rate related intervals." Furthermore, the same method of extracting RSA waves from pp intervals can be directly applied to these other points as well. Preferred embodiments of the present invention, however, parse waves within pp interval data sets.

Figure 3:
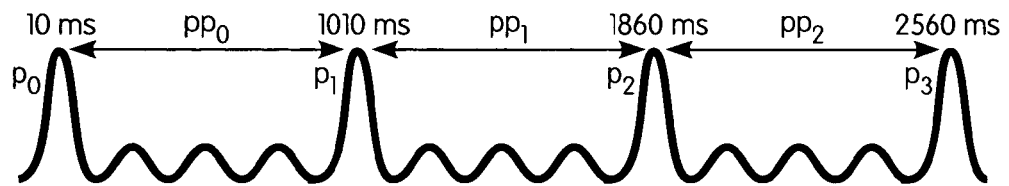
FIG. 3 illustrates an exemplary series of RSA waves and calculates the interbeat interval times (IBI) between successive pulse peaks.

The pulse rate of each recorded pp interval (60,000/pp) may be displayed on the screen each time a new pulse peak is encountered. The absolute time difference between successive pp intervals (absolute (pp[n]−pp[n−1])) is called the interbeat interval time (IBI) (FIG. 3). An aspect of the present invention uses the pp interval times to identify individual RSA waves. The methods described herein may be used for both spontaneous and guided breathing.

Figure 4A:
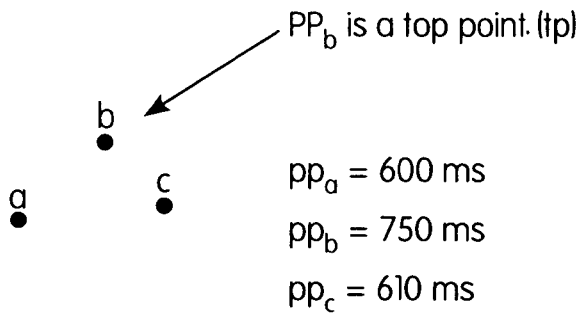
FIGS. 4a-d identify, respectively, a representative top point, bottom point, ascending transition point and descending transition point.
Figure 4B:
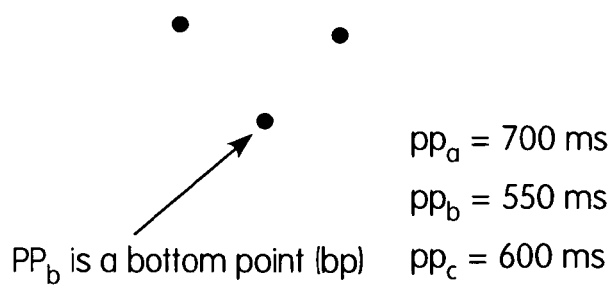
Figure 4C:
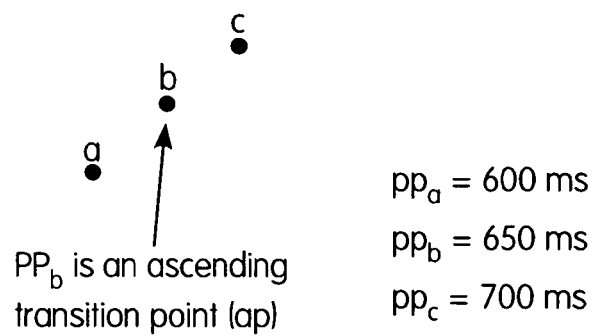
Figure 4D:
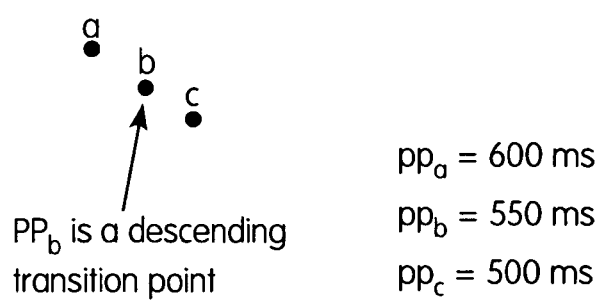
Figure 5:
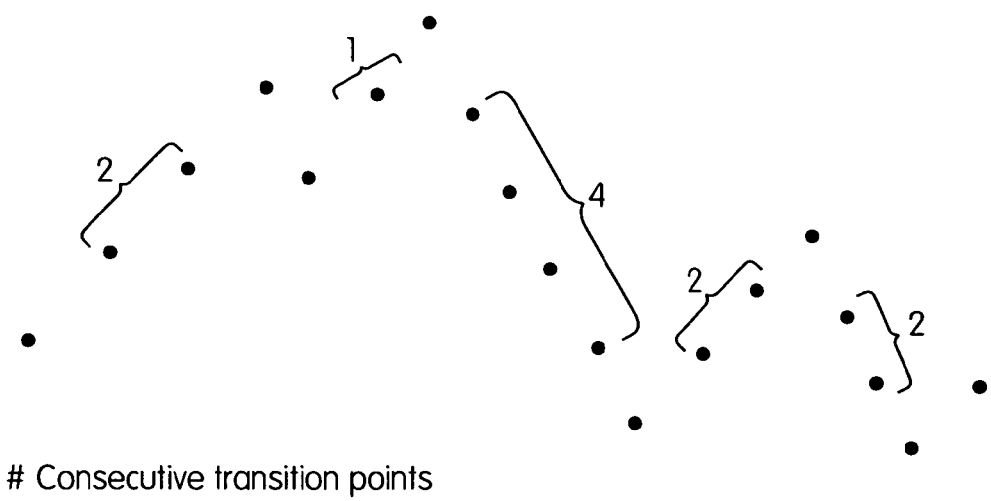
FIG. 5 illustrates representative consecutive ascending and descending transition points.

Each p-p may be categorized by examining its relationship to the p-p immediately before it (the previous pp) and the p-p immediately after it (the next p-p). A p-p may be considered a top point (tp) if the previous p-p is equal to or less than it and the next p-p is equal to or less than it as well (FIG. 4a). A p-p may be considered a bottom point (bp) if the previous p-p is equal to or greater then it and the next p-p is equal to or greater than it as well (FIG. 4b). A p-p may be considered an ascending transition point (at) if the previous p-p is less than it and the next p-p is greater than it (FIG. 4c). A p-p may be considered a descending transition point (dt) if the previous p-p is greater than it and the next p-p is less than it (FIG. 4d). Thus, a p-p may be categorized as either a top point (tp), bottom point (bp), ascending transition point (at), or descending transition point (dt). The "term transition point" can be used to refer to both ascending and descending transition points when it is not qualified with the words "ascending" or "descending". Consecutive transition points refers to a series of consecutive ascending transition points or descending transition points (FIG. 5).

Figure 6:
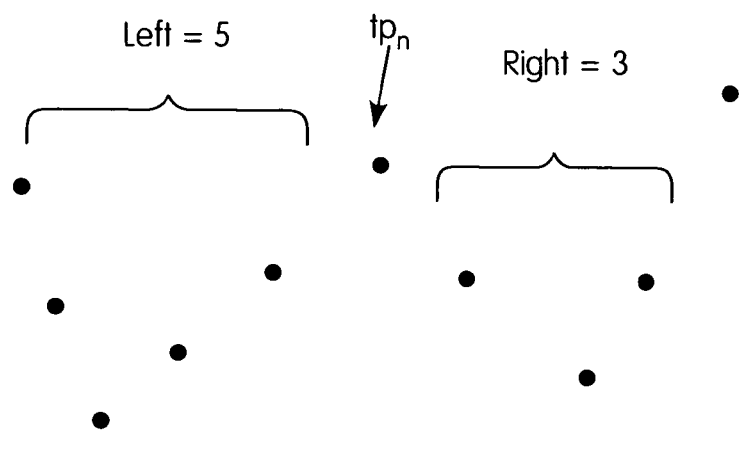
FIG. 6 illustrates an exemplary method for identifying a top point.
Figure 37:
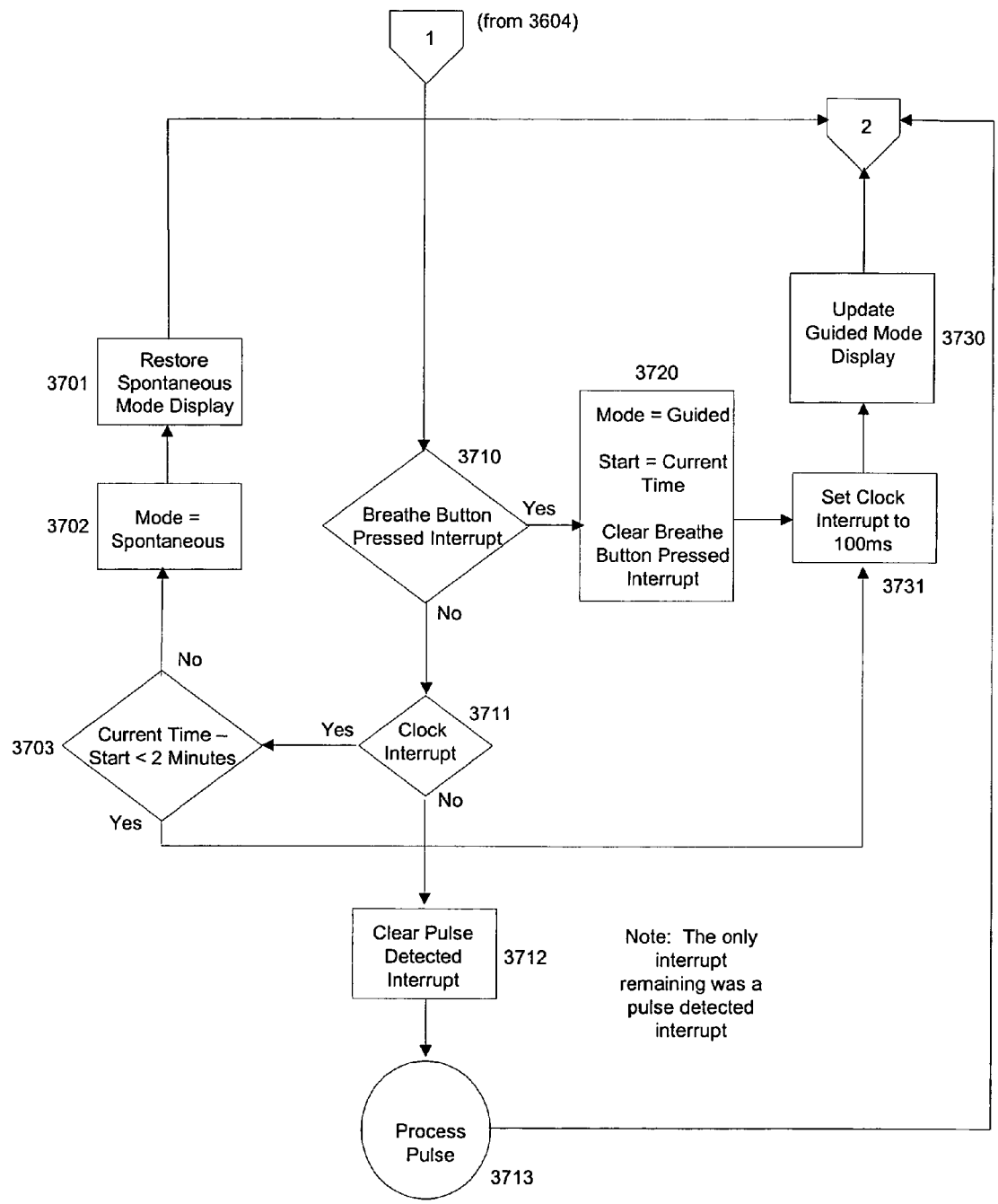

The term "top level" may be used to refer to the relative height of the top point. The level of a top point may be computed as follows. L=the number of consecutive points immediately to the left of the top point that are less than or equal to the top point. R=the number of consecutive points immediately to the right of the top point that are less than or equal to the top point. If L<R, then the top level is equal to L, otherwise the level of the top is equal to R. FIG. 37/FIG. 6 illustrates, using three examples, how the top point level may be categorized.

Figure 7:
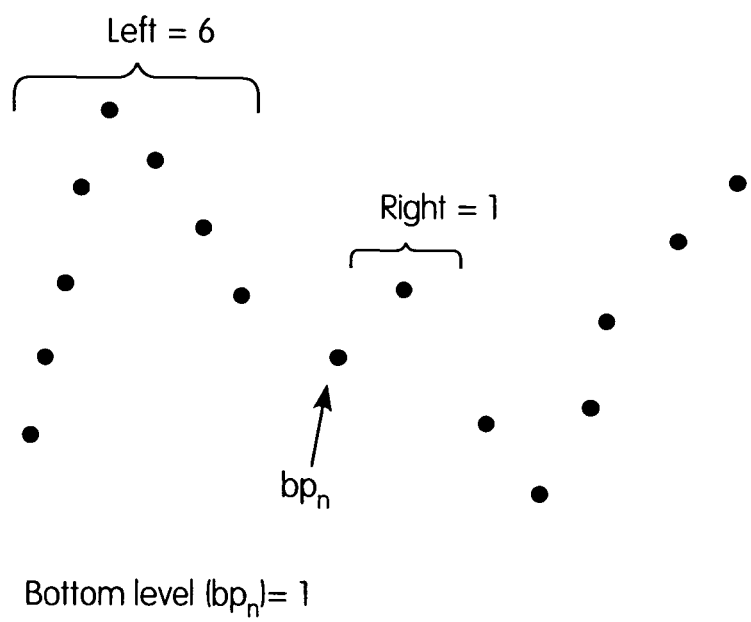
FIG. 7 illustrates an exemplary method for identifying a bottom point.

The term "bottom level" may be used to refer to the relative height of the bottom point. The level of a bottom point may be computed as follows. L=the number of consecutive points immediately to the left of the bottom point that are greater than or equal to the bottom point. R=the number of consecutive points immediately to the right of the bottom point that are greater than or equal to the bottom point. If L<R then the bottom level is equal to L otherwise the level of the bottom is equal to R. FIG. 7 illustrates, using three examples, how the bottom point level may be categorized.

Figure 8A:
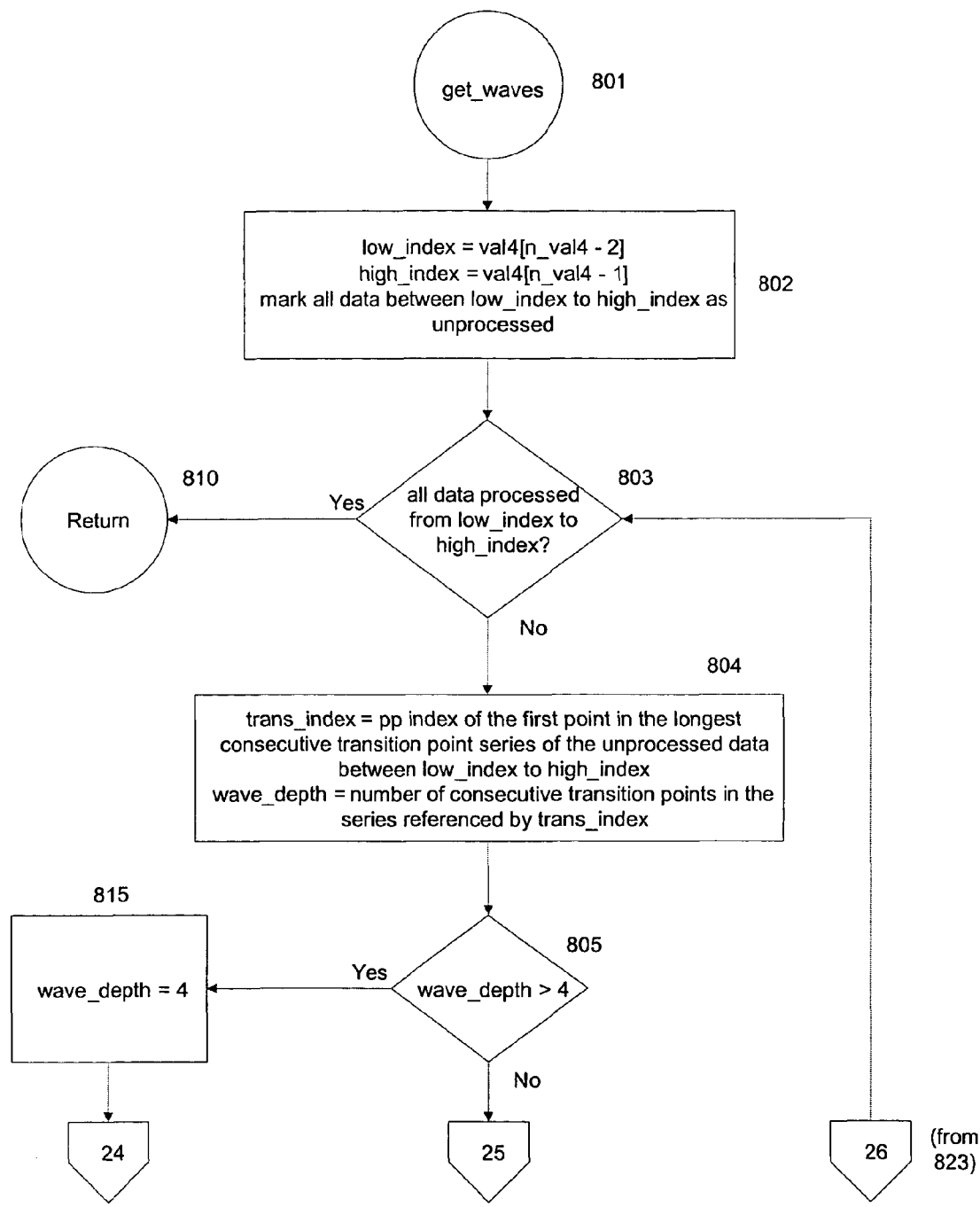
FIGS. 8(a)-(b) depict an exemplary process flow for an exemplary procedure for finding RSA waves within a data set according to an exemplary embodiment of the present invention.
Figure 8B:
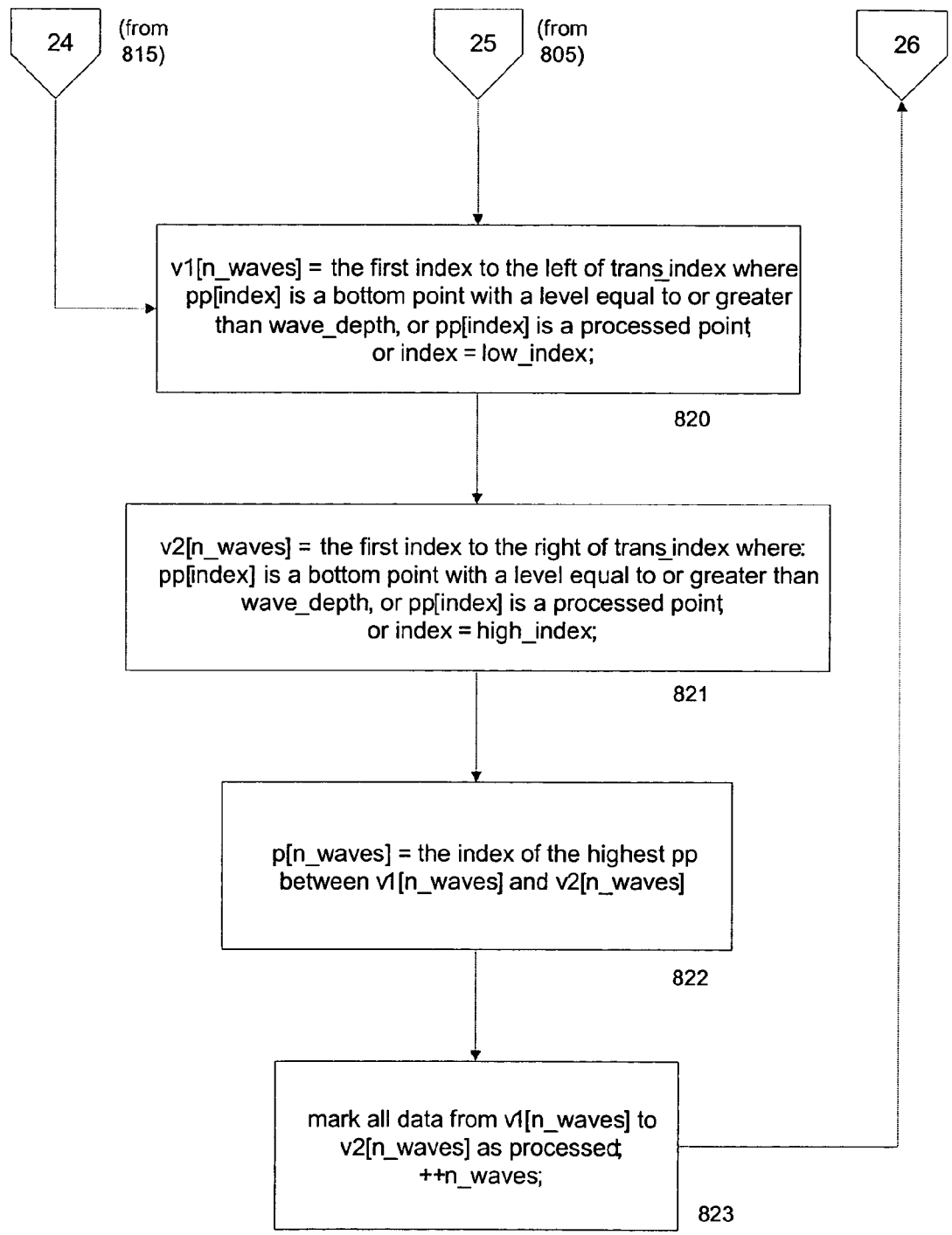
Figure 9:
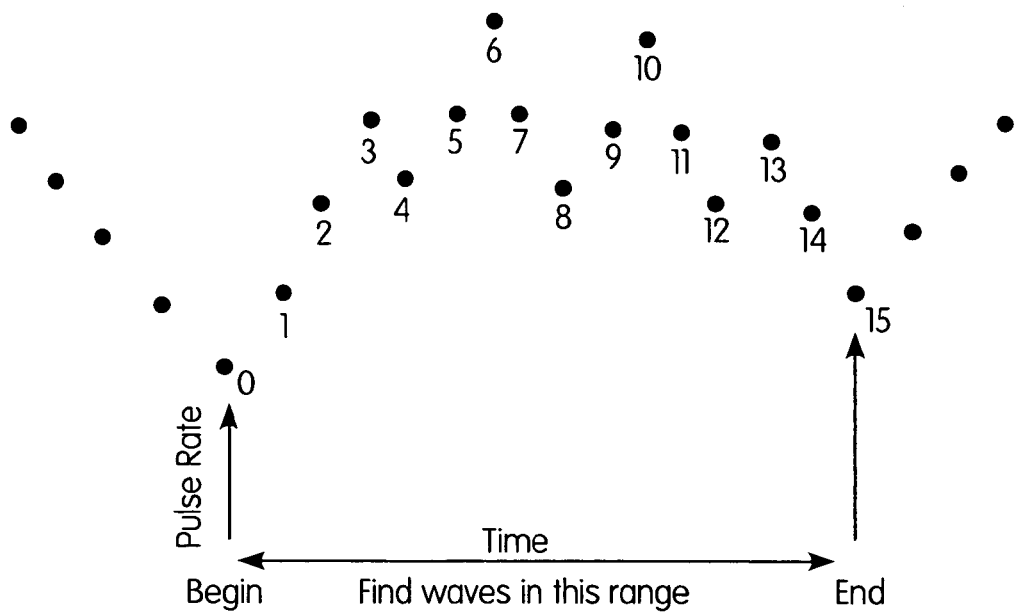
FIG. 9 illustrates an exemplary procedure for identifying RSA waves within a data set.

FIGS. 8(a)-(b) provide an exemplary flowchart which illustrates an exemplary procedure for finding the RSA waves within a data set while FIG. 9 illustrates how this procedure may be applied. In an exemplary embodiment of the present invention, the first step is to locate the highest number of consecutive transition points (ctp) in the data set. In FIG. 9 the highest number of consecutive transition points begins at point 1. There are 2 consecutive transition points. The wave depth is equal to the number of these transition points. Thus, the wave depth in this example is 2. In preferred embodiments, if the wave depth is greater than 4, the wave depth value is adjusted down to 4.

Figure 40:
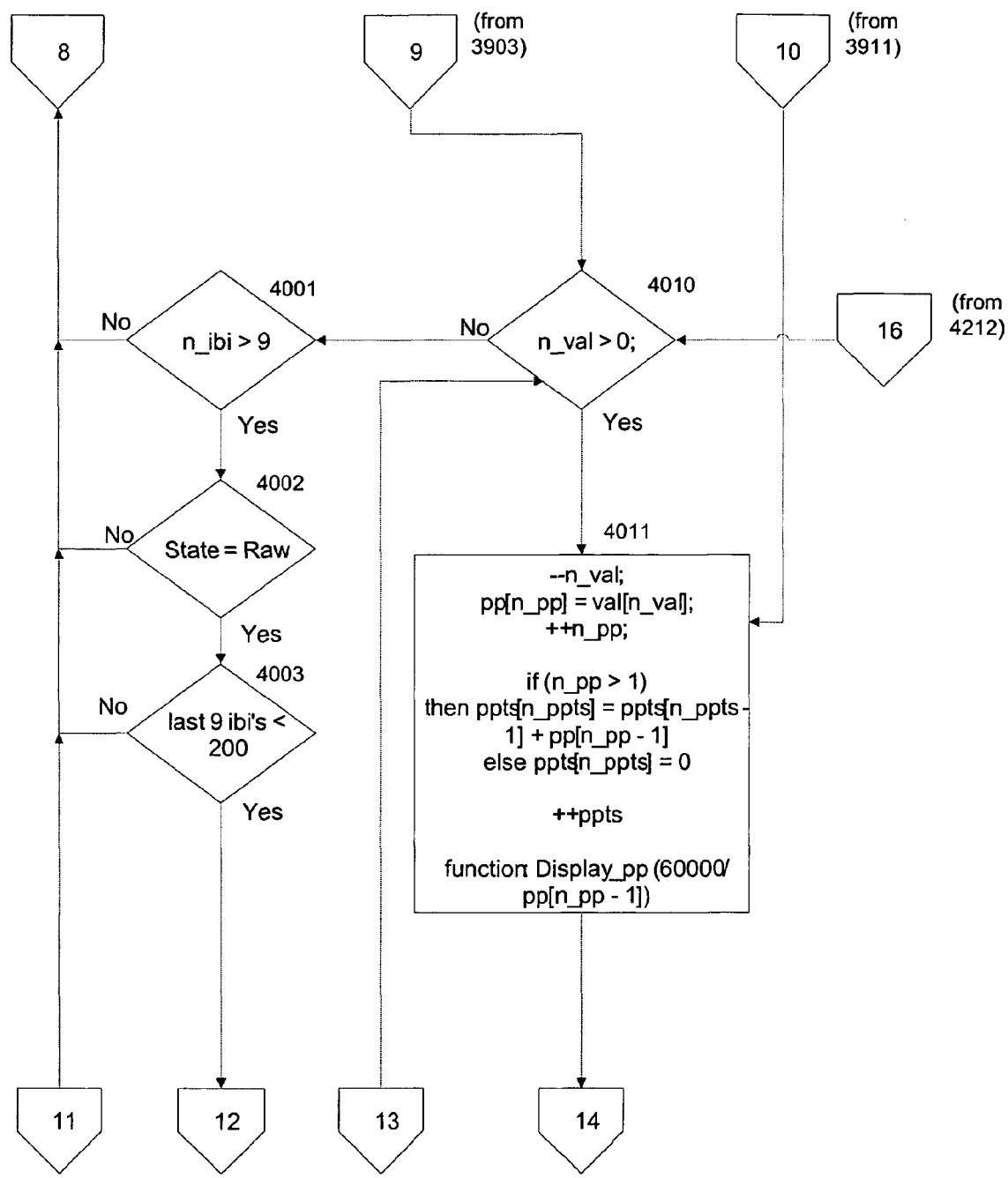
Figure 41:
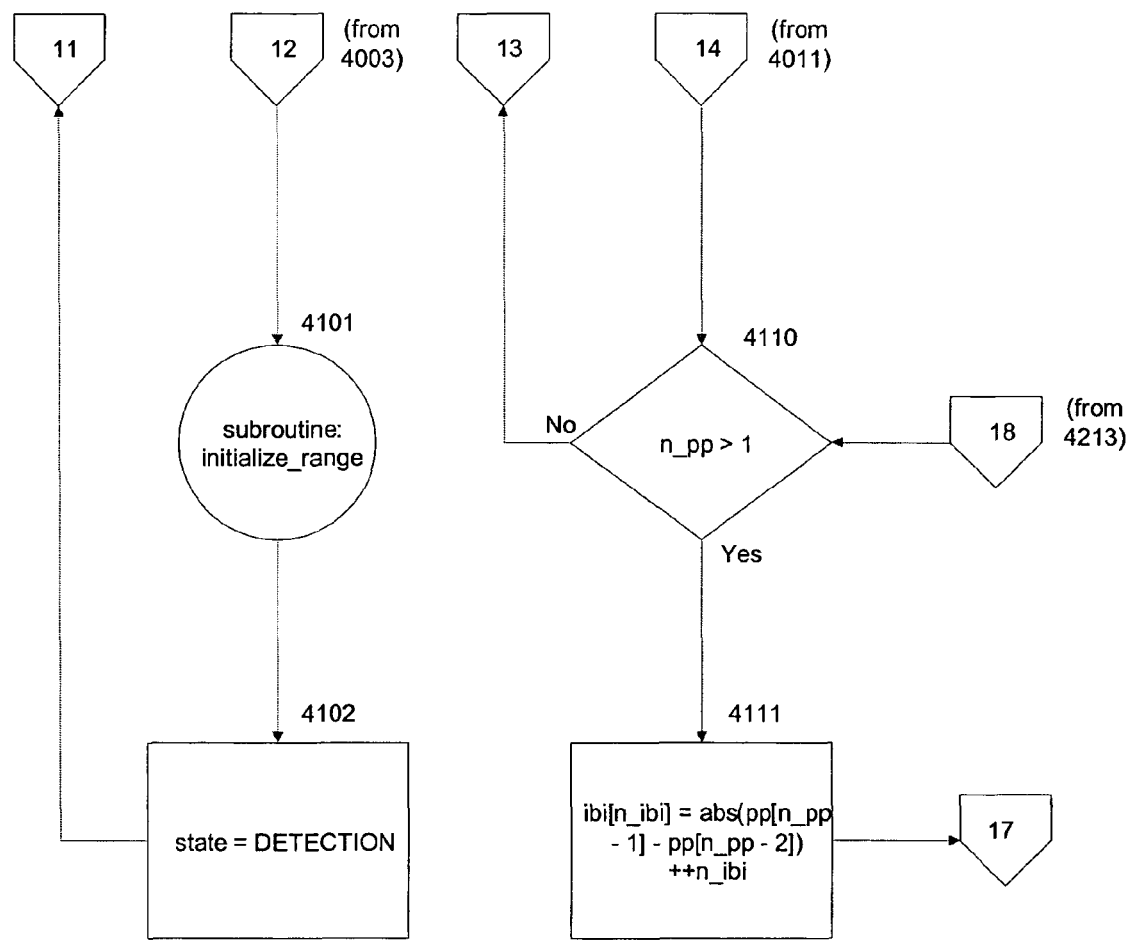
Figure 42:
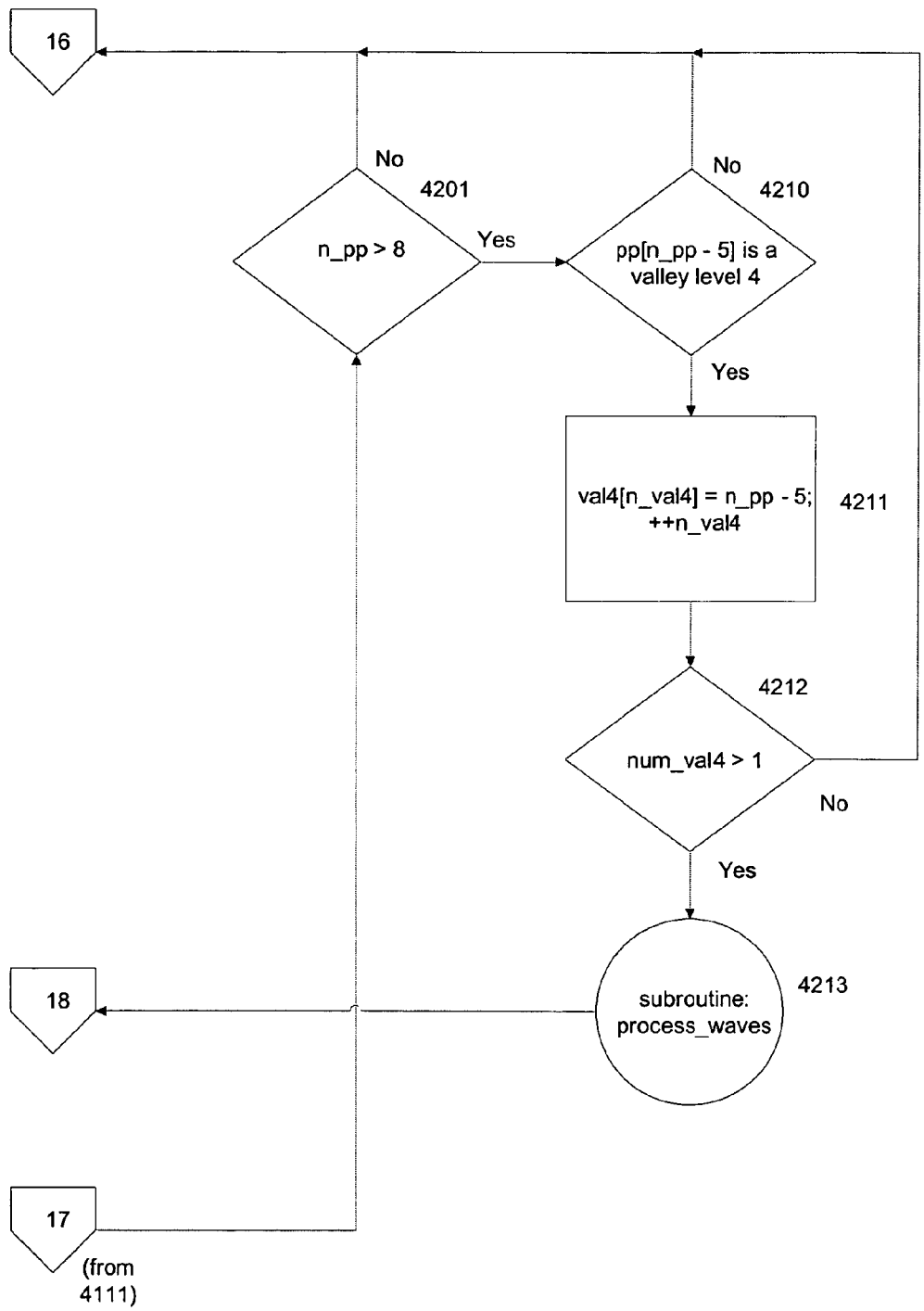

The next step is to locate the bottom point to the right of the consecutive transition points where the bottom level is equal to or greater than the wave depth. This is the right valley point (v2) of the RSA wave. In the example in FIG. 9, bottom point no. 8 has a level of 3, which is greater than the wave depth. The next step is to locate the bottom point to the right of the consecutive transition points where the bottom level is equal to or greater than the wave depth. This is the left valley point (v1) of the RSA wave. In the example provided in FIG. 9, bottom point no. 0 has a level 4, which is greater than the wave length. The next step is to find the highest point between the left valley point and the right valley point. This is the peak (p) of the RSA wave. In the example in FIG. 40/FIG. 9, point 6 is the highest point between the two valley points. All data from the left valley point (v1) to the right valley point (v2) is considered processed data. The same procedure is repeated on the remaining unprocessed data until all possible waves have been identified.

There are a number of variations in the method described above which should be considered within the scope of the present invention. For example, a similar method could be used to find peaks on each side of a transition point series. The valley between two peak points would therefore be the lowest point between the two peaks. Also, wave depth may be based on the absolute number of transition points or a derived number based upon the number of transition points (e.g., number of transition points×75%). Also, the v1 point could be identified before the v2 point.

In preferred embodiments, the wave parsing method discussed above is used each time a new bottom level 4 point is identified. Thus, devices according to exemplary embodiments of the present invention "look" for RSA waves between bottom level 4 points. In other exemplary embodiments, devices may be configured to "look" for RSA waves after each point, or after a certain period of time elapses (every 30 seconds for example), etc. Exemplary embodiments use bottom level 4 points because they have a very high probability of delineating RSA waves. That is, they have a high probability of being valley points (v1, v2) of RSA waves.

Figure 10:
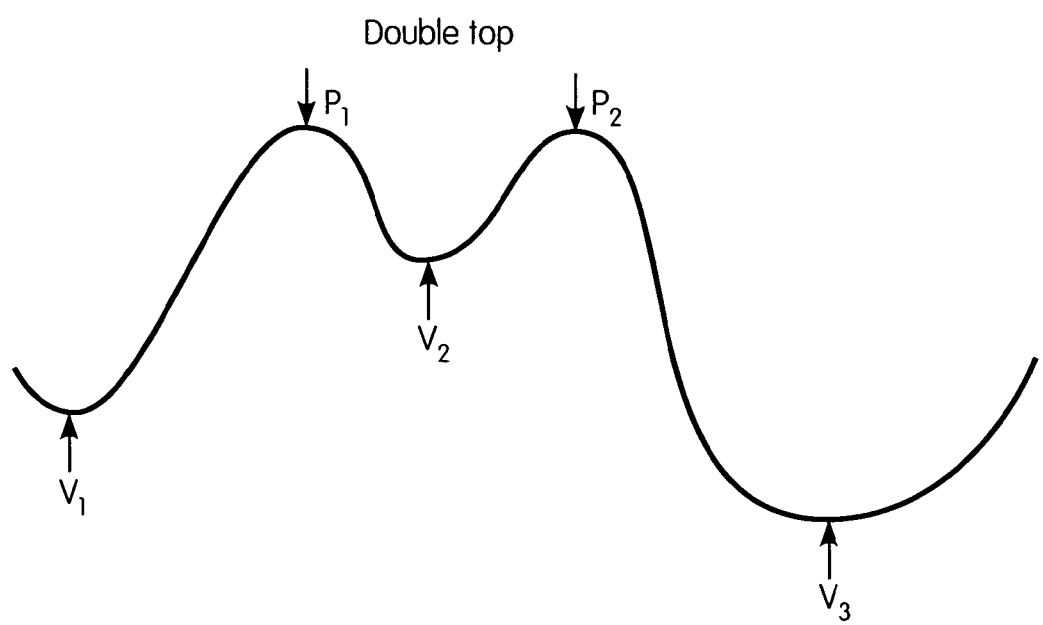
FIG. 10 illustrates an exemplary double top wave.

There are two instances where the basic RSA wave parsing methods described above may inaccurately describe an RSA wave. One may occur when a double top wave is encountered. Double top waves may be formed when a person waits a long time to inhale after he or she has already exhaled. Another may occur when double bottom waves are formed. Double bottom waves may be formed when a person holds his breath for a long time after inhaling. Double tops are easily identified by examining the ratios of lengths of the two waves (FIG. 10). When (p1-v2) is much smaller than (p1-v1), and (p2-v2) is much smaller than (p2-v3), and (p1-v2) is very close to (p2-v3) then a double top has occurred. In preferred embodiments, double tops may be defined as situations where: ((p1-v2)/(p1-v2))<0.50 and ((p2-v2)/(p2-v3))<0.50 and ((p1-v1)/(p2-v3))>0.75. Double bottoms may be defined as the inverse of double tops.

Figure 11:
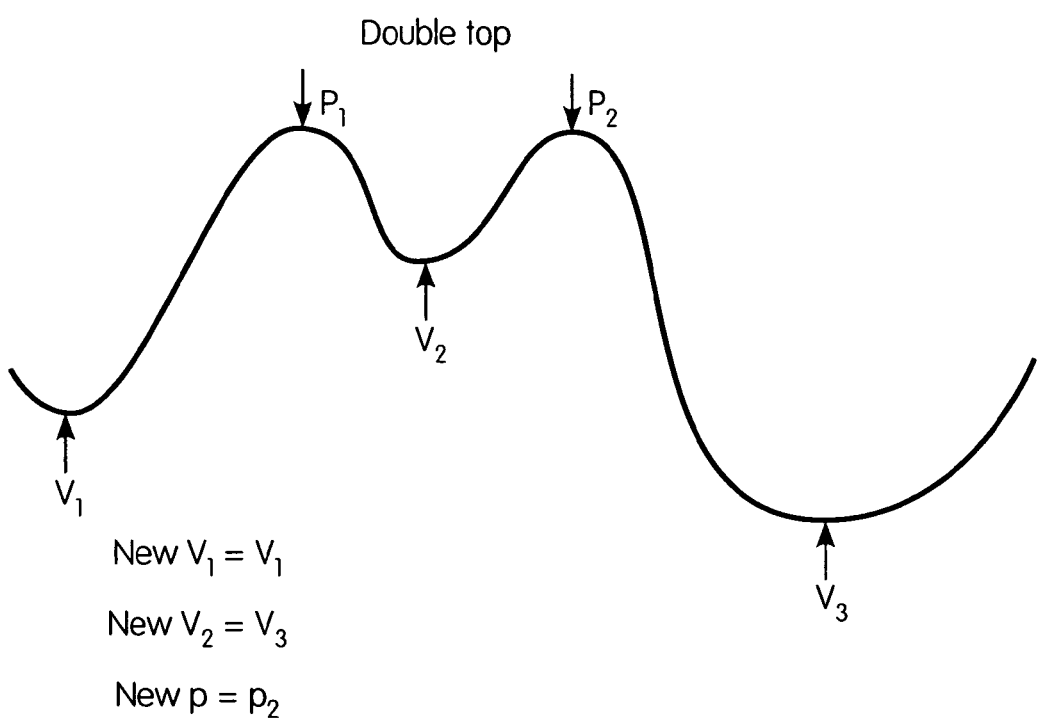
FIG. 11 illustrates an exemplary method for correcting data from a representative double top wave.

Whenever double tops or double bottoms are produced from the basic parsing method, the two waves forming the pattern may be merged together into one wave. Point v1 is the v1 of the new wave. Point v3 becomes the v2 of the new wave. The highest value between v1 and v3 is the peak point of the new wave. This is illustrated by FIG. 11.

Use of RSA Waves to Analyze and Reduce Stress

Exemplary embodiments of the present invention can use the RSA wave information described above to assess the user's level of mental stress. This mental stress measurement may be presented in devices as a stress meter (FIG. 12(5)). For example, when a person is stressed, breathing usually becomes rapid and irregular, relative to a non-stressed state. This rapid, irregular breathing can cause the formation of short, choppy RSA waves. Methods and devices according to the present invention can be used to determine the user's stress level by determining how far the user's average wavelengths deviate from a level that represents a relaxed state. Such methods and devices also may compute how irregular (arrhythmic) the user's waves are. These two assessments may be used individually or combined into a single value to indicate the overall stress level.

Studies have demonstrated that when people are profoundly relaxed (such as in a state of deep meditation), they tend to breathe in a steady rhythm at approximately 6 breaths per minute. Such rhythmic breathing causes the RSA wavelengths to become entrained on the breathing frequency. Thus, rhythmic breathing at 6 breaths per minute will result in a series of RSA waves having wavelengths of 10 seconds. Thus, exemplary embodiments of the present invention use wavelengths of 10 seconds as the relaxation threshold when assessing the user's stress level. Exemplary embodiments also include methods and devices which compute the average wavelength of the last five waves to determine how far the average is, proportionally, from 10 seconds. This is one example of a "wavelength score".

Arrhythmic waves may be quantified using a number of standard variance formulas. Exemplary embodiments of the present invention use the sum of the differences of each consecutive wavelength in the last five waves to compute a "variance score". Exemplary embodiments also can use the sum of the differences between successive wavelengths and may use a rank order weighted averaging so that the variance of the most recent waves count more. The stress level in an exemplary embodiment of the present invention uses 70% of the "wavelength score"+30% of the "variance score". The user's stress level can be recalculated each time a new RSA wave is identified.

Stress can cause a variety of RSA wave behaviors: decreased peak to peak times, increased peak to peak frequency, decreased wavelength, increased wave frequency, decreased amplitude, irregular wavelengths, irregular wave frequencies, irregular amplitudes, irregular peak to peak times, irregular peak to peak frequencies, irregular peak placements or decreased variation. Any one of the preceding variables, or any combinations thereof, can be applied to RSA waves and used as an indicator of the level of stress. Identifying individual RSA waves and using any of the preceding variables alone, in combination with each other, and/or in combination with other variables, to evaluate stress is within the scope of the present invention and has not been described in the prior art.

In addition to using the identified RSA waves for determining stress levels, devices and methods according to exemplary embodiments of the present invention can also use RSA wave information to determine and display both average heart rate and wave frequency. The average of all the pulse rates in the last wave may be used to assess average heart rate. For example, each time a new RSA wave is identified, the average of the pulse rates may be computed and the heart rate may be updated. The wave frequency display also may be updated every time that a new RSA wave is identified. Exemplary embodiments can express frequency relative to waves (breaths) per minute. In exemplary embodiments the wave frequency and heart rate may be rounded to the nearest integer.

Exemplary Device

The description below relates to a particular exemplary embodiment of the present invention in the form of a device which may be used to evaluate stress in humans. In this exemplary embodiment, RSA waves may be identified as described above and used to provide biofeedback to a user. In addition to the particular exemplary embodiment described below, it should be appreciated that other methods and devices are intended to be within the scope of the present invention. Alternative embodiments are occasionally described under this section. Where alternative embodiments are not explicitly described, it is not the intention of applicants to limit the present invention to the exact description provided in this section. The full scope of the present invention is based on the disclosure in the specification as a whole.

Figure 13:
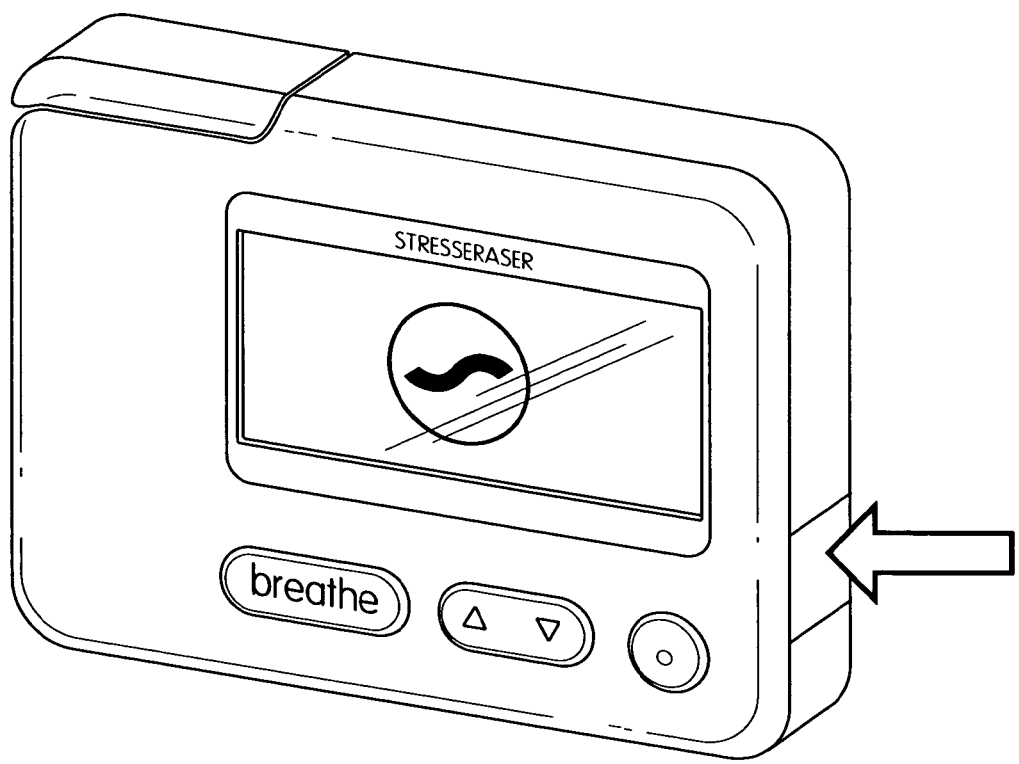
FIG. 13 illustrates an exemplary embodiment of a device in accordance with the present invention and identifies a potential location for a power switch.
Figure 14:
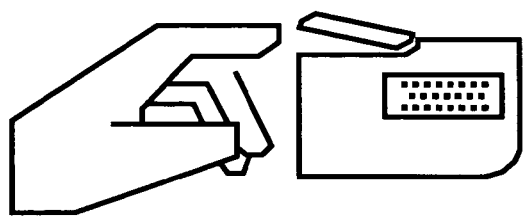
FIG. 14 illustrates a representative location for a PPG sensor which can collect data from a subject's finger.
Figure 15A:
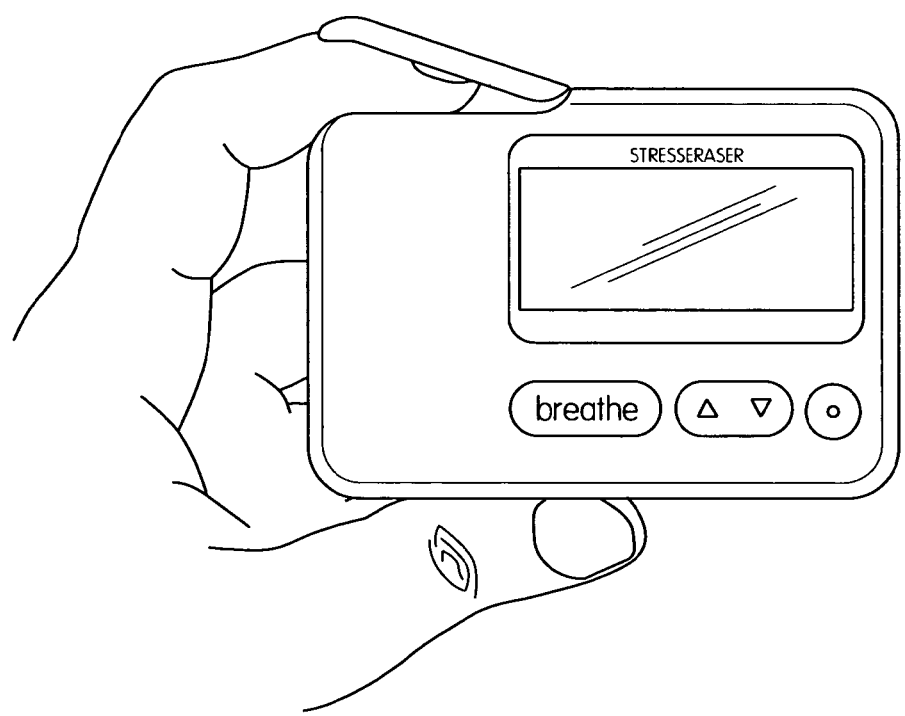
FIG. 15a-b illustrates alternate methods for a subject to hold an exemplary device while the subject's finger is in the PPG sensor.
Figure 15B:
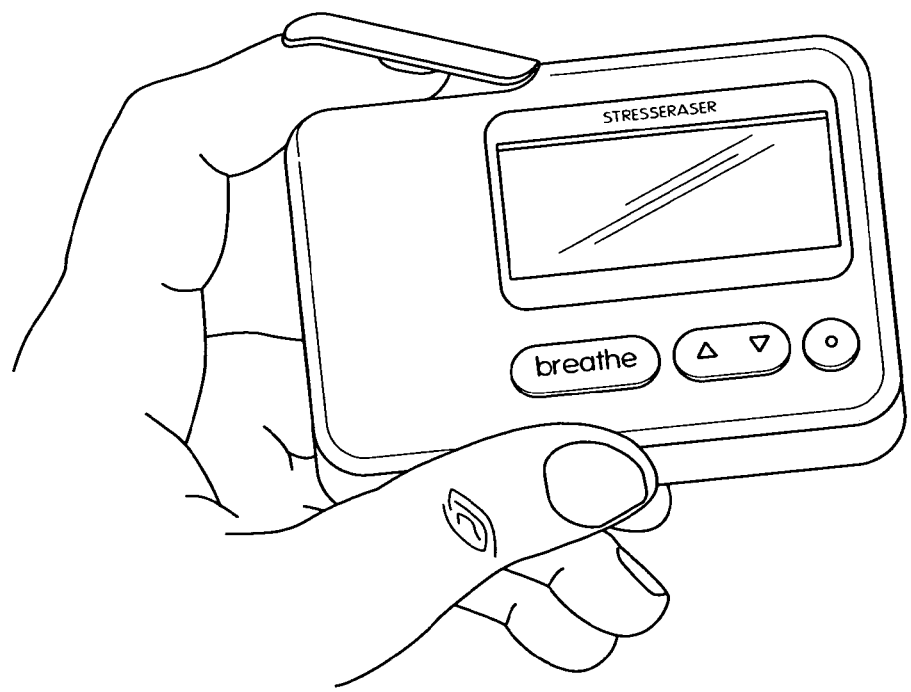

The present invention includes, for example, a battery powered handheld portable device including a PPG sensor, a display screen, control buttons, and a power button (FIG. 13). The user can turn on the device by pressing a power button. If the device is being used in a dark room, the user can turn on backlighting by pressing the power button a second time and keeping it pressed for a few seconds. Soon after the device has been powered on, it prompts the user to insert a finger into the finger sensor (/FIG. 14). The user then gently holds the device with a finger resting on top of the sensor throughout the entire session. The device can be comfortably held vertically, resting on the thumb (FIG. 15a) or at an angle, resting on the curled fingers of the hand holding it (FIG. 15b).

Figure 16:
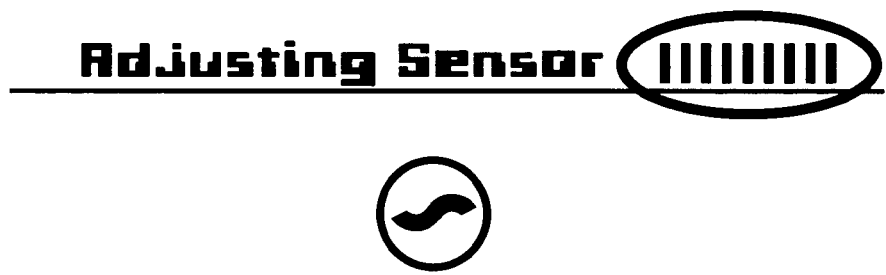
FIG. 16 illustrates an exemplary display of a countdown meter.
Figure 17:
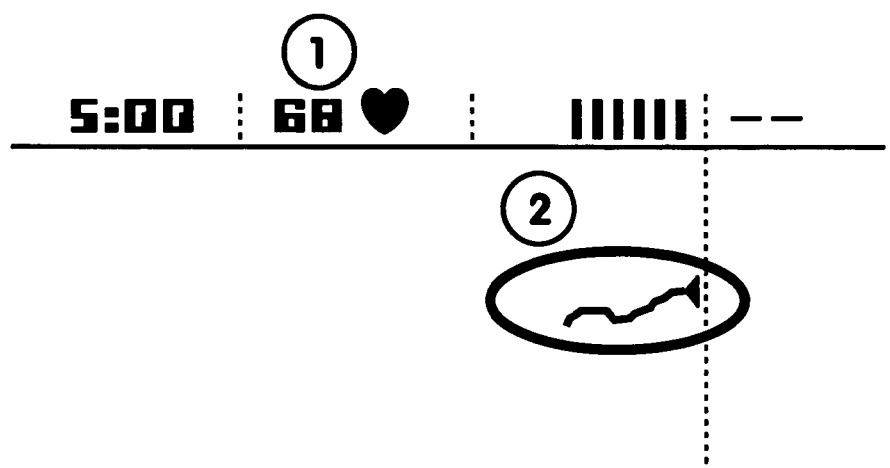
FIG. 17 illustrates an exemplary display of a representative average pulse rate as well as a pulse rate over time.

Once the finger has been inserted into the finger sensor, the device then begins to calibrate the PPG sensor. A countdown meter marks the amount of time required for the calibration (FIG. 16). After the PPG sensor is calibrated, the device uses the PPG sensor to detect each pulse of blood in the finger. The resulting pulse rate (60,000/number of milliseconds between two consecutive pulse peaks) is then plotted on the screen on a pulse by pulse basis (FIG. 17(2)). The display also shows the user his average pulse rate (FIG. 17(1)).

Figure 18:
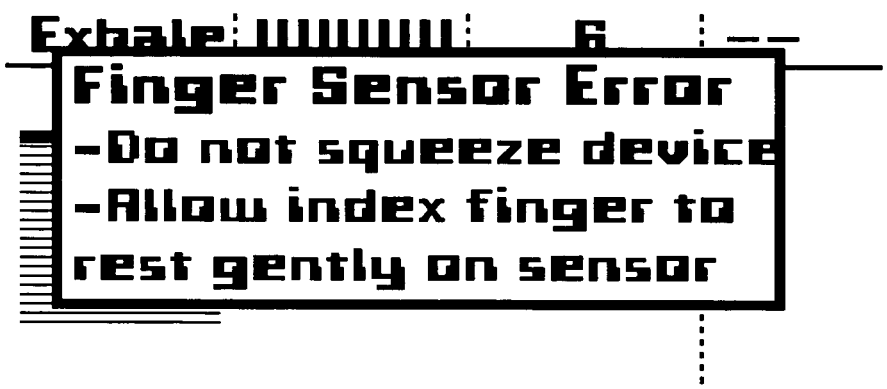
FIG. 18 illustrates an exemplary display of an error message.

PPG sensors can be very sensitive to finger pressure. That is, if the user is squeezing the device, the resulting finger pressure may prevent the device from gathering accurate pulse rate information. Whenever the user applies too much pressure, the device will display an error message alerting the user to stop squeezing the device and start to relax his finger (FIG. 18). As soon as the user has successfully relaxed his finger, he is then returned to the pulse rate display screen.

Figure 12:
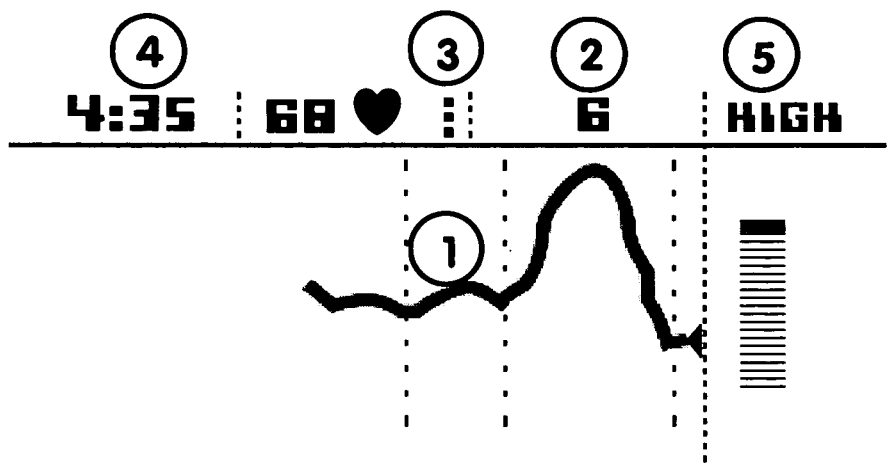
FIG. 12 illustrates an exemplary display of a stress meter.

When the device identifies a new RSA wave, it uses the wave information to determine and display five things: the frequency of the last wave, the average pulse rate of all the pulse points in the wave, the session score, the remaining session time and the stress index—how much mental stress the user is currently experiencing (FIG. 12).

The device updates the session countdown clock after every RSA wave has been identified. An alternative exemplary embodiment could include a session countdown clock that decrements on a regular basis (e.g., once per second, once every fifteen seconds, etc.). In this exemplary embodiment, the device updates after each RSA wave to avoid unconscious associations being made between the clock and the desired behavior. In other words, if the clock counted down on a per second basis, the user could consciously or unconsciously use the seconds as a guide to breathing at the rate of 6 breaths per minute. Such an association may prevent the user from unconsciously learning how to breathe at 6 breaths per minute whenever becoming stressed. If the user consciously (or even unconsciously) uses the clock, he or she may always be dependent on the device. However, by updating the clock based upon every wave, such a potential situation is not only avoided, but the clock can reinforce the learning. The user will see the exact number of seconds of each breath by the amount that the clock decrements. If the clock were to decrement more slowly (e.g., once every 30 seconds), the potential for unconscious associations between time and desired behavior would be avoided. However, in such an alternative implementation, the clock would not be reinforcing the learning.

Figure 19:
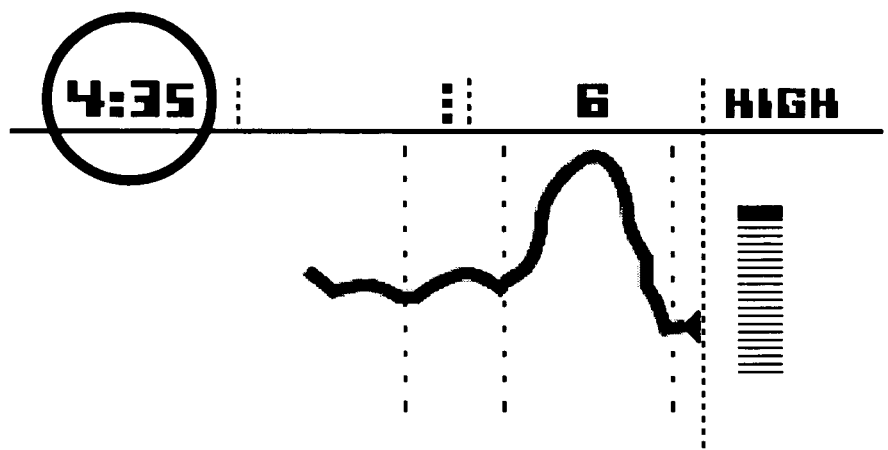
FIG. 19 illustrates an exemplary embodiment of a countdown timer.

In this exemplary embodiment, the session countdown timer begins to decrement once the first wave is identified and data is displayed (FIG. 19). However, alternative embodiments could begin decrementing the counter when the user begins to breathe rhythmically, or only when they good waves are achieved (e.g., waves with a frequency less than six), or only while the user is practicing rhythmic breathing. Another alternative is to not decrement the counter when the breathe button is being used and guidance is being provided.

Figure 20:
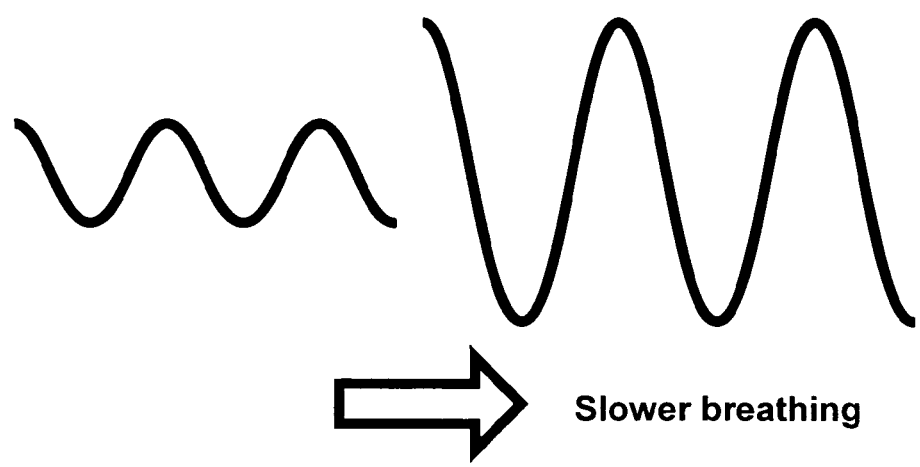
FIG. 20 provides a representative illustration of RSA waves of a subject whose breathing has slowed over time.
Figure 21:
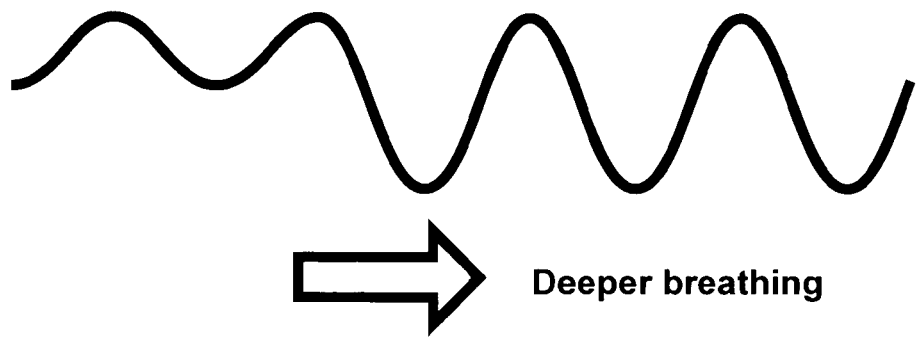
FIG. 21 provides a representative illustration of RSA waves of a subject who has taken deeper breaths over time.
Figure 22:
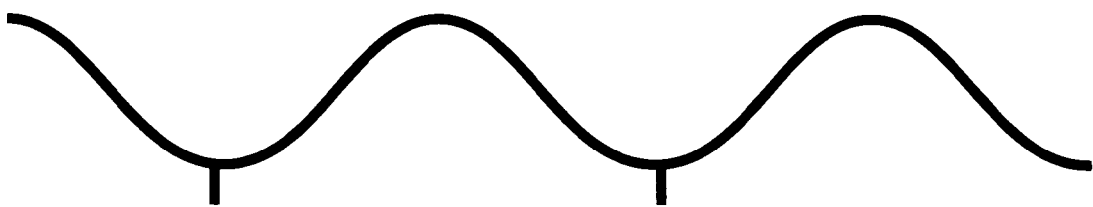
FIG. 22 illustrates a representative RSA pattern consistent with rhythmic breathing.

Users can alter the behavior of the waves, and therefore their calculated stress level, by changing their breathing pattern. As the user slows down his rate of breathing, the wavelengths increase and the amplitude of the waves increases as well (FIG. 20). When a person breathes more deeply, the amplitude of the waves becomes even larger (FIG. 21). When a person breathes rhythmically at a steady rate, the wavelengths entrain on the breathing rate (FIG. 22).

Figure 23:
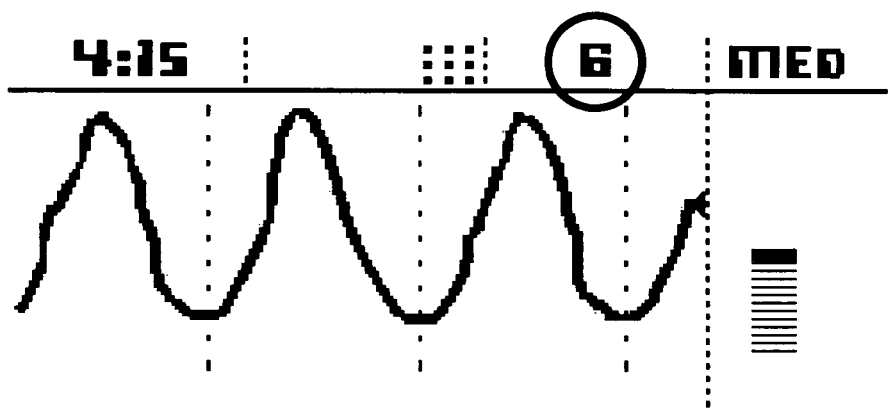
FIG. 23 provides a representative display of a subject with a wave frequency of six.

The first step in using the device to relax is to inhale deeply and then slowly let the air out, extending exhalation. This will cause the wave lengths to become longer and therefore the frequency of the waves to decrease. The user continues to inhale deeply and to slow exhalation even more until the wave frequency drops to 6 (FIG. 16/FIG. 23). If the wave frequency drops below six, then the user will need to breathe a little faster—that is, not exhale quite as long next time.

Figure 24:
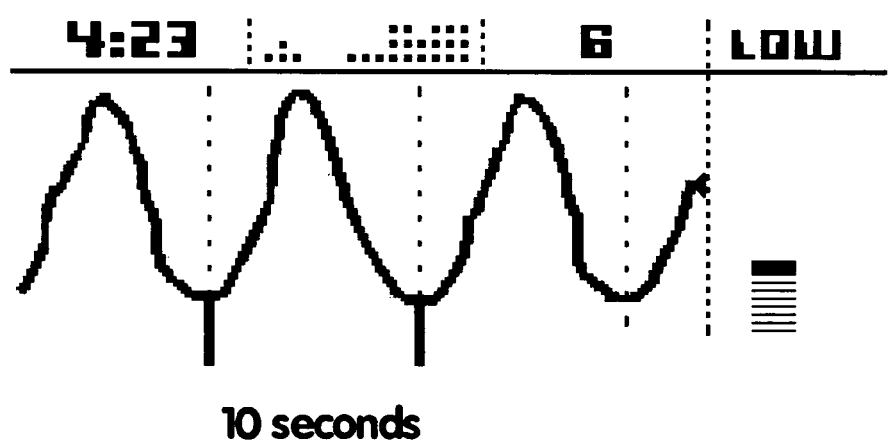
FIG. 24 provides another representative display of a subject with a wave frequency of six.

Once the user has reduced the wave frequency to 6, he or she continues breathing at the same rate and rhythm that produced a frequency of 6. If the user's breathing rate increases, the frequency will increase, indicating that his next breath needs to have a longer exhalation. If the user's breathing rate becomes too slow, the frequency will drop below 6; indicating that the exhalation of the next breath needs to be a little faster. By paying attention to the wave frequency number, a user can quickly fill the screen with rhythmic waves that are 10 seconds in length (FIG. 24) corresponding to a frequency of 6 respiration cycles per minute.

Figure 25:
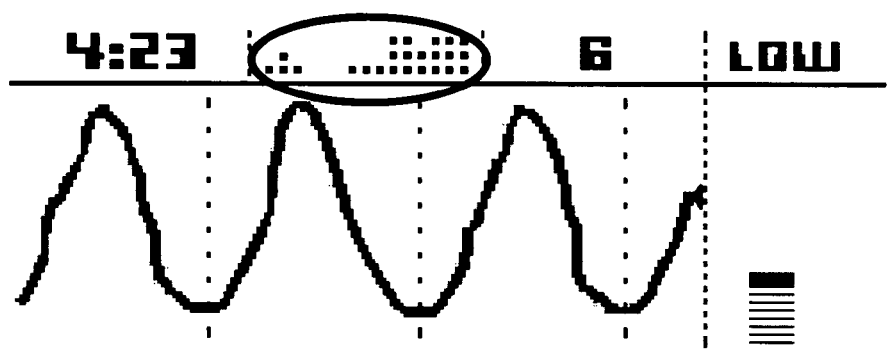
FIG. 25 illustrates an exemplary display of a session score for a subject.

The session score is calculated and displayed after each RSA wave is identified. The score is based upon how close the user is to achieving the desired behavior. The user accumulates score points. Various methods for scoring the session may be used. In certain embodiments, the user receives 3 points if the waves have a frequency of 6 or less. The user receives two points for wave frequencies of 7 or 8, one point for wave frequencies of 9 or 10 and no points for frequencies greater than 10. The accumulated session score could be displayed numerically. Alternatively, each individual score could be displayed. Yet another alternative is to show the current score along side a set of the previous scores (either numerically or graphically). Preferred embodiments graphically display the current score and a set of the previous scores (FIG. 25). In this way, the user can tell when he is breathing rhythmically. When the score display is uniform, the user is breathing rhythmically.

Figure 26:
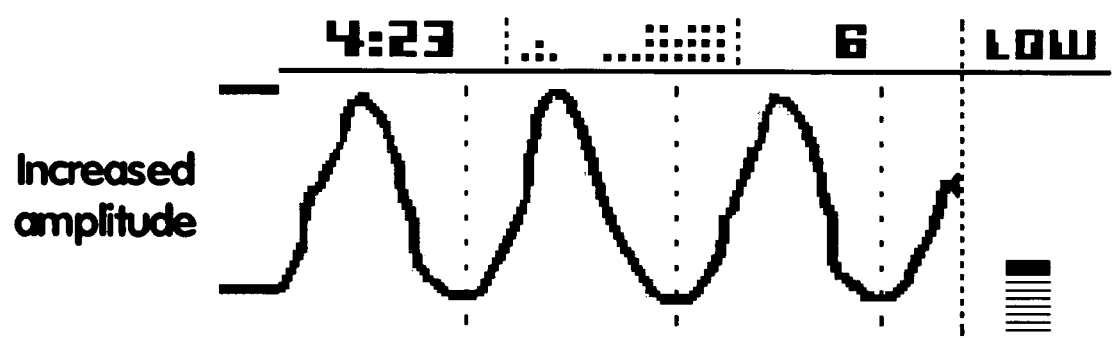
FIG. 26 illustrates an exemplary display of a subject whose depth of breathing has increased and is generated relatively large waves with a duration of about 10 seconds each.

Once the user has filled the screen with rhythmic waves, he should focus on inhaling a little more deeply, and exhaling a little more fully. That is, the user should try to inhale and exhale a greater volume of air (called tidal volume). As the user gently increases the depth of his breathing, the size of the waves will increase (FIG. 26). The user continues to fill the screen with large waves whose wavelengths are 10 seconds each until the session timer runs out. The user will then find that he has achieved a very deep and profound state of relaxation.

Figure 27:
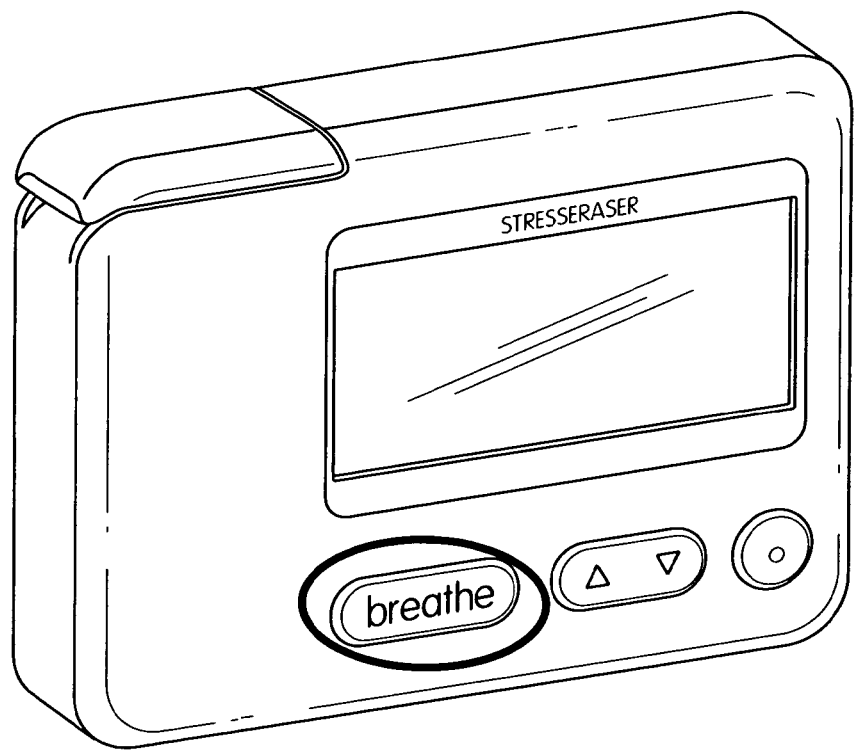
FIG. 27 illustrates a representative location for a guided breathing switch for activating a guided breathing function in exemplary devices of the present invention.
Figure 28A:
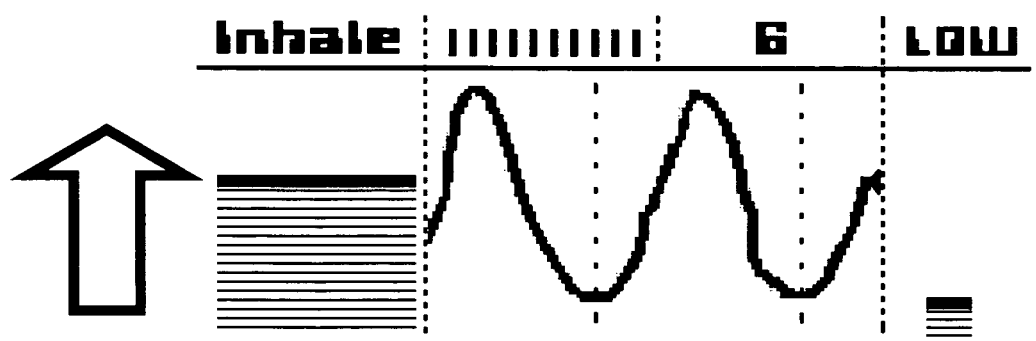
FIG. 28a-b illustrate an exemplary display for guided breathing with a breathing bar that increases to guide inhalation and decreases to guide exhalation.
Figure 28B:
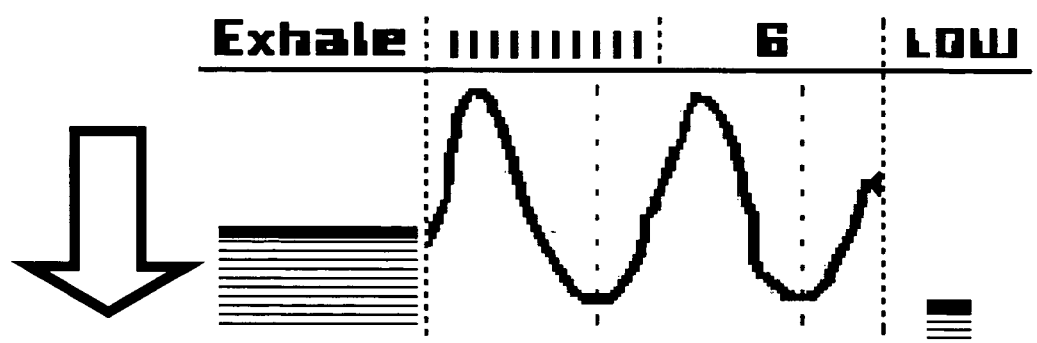

If a user has difficulty breathing deeply and rhythmically at a rate of 6 breaths per minute he can obtain guidance by activating a breathing guide function. (FIG. 27). As soon as the user presses the breathe button, a breathing guide appears on the display. The user is instructed to inhale as the breathing bar rises (FIG. 21a/FIG. 28a) and exhale as the breathing bar descends (FIG. 21b/FIG. 28b). In exemplary embodiments, the breathing guide paces the user's breathing to 6 breaths per minute with, for example, a 1:2 ratio of inhale:exhale. In alternative embodiments, the breathing guide could be programmed to provide other rhythms (e.g., 1:3) at a ration close to 6 breaths per minute (e.g., 4-8/minute). The breathing guide remains active for one minute, automatically shutting off thereafter. By having a temporary, rather than constant, breathing guide, the user is encouraged to use the biofeedback protocol to achieve the six breaths per minute respiration pattern. If the user were to rely solely on the breathing guide, it would be much more difficult to learn how to achieve the pattern on his own. Thus, by weaning the user off the breathing guide, the user is able to use biofeedback to create unconscious learning. An alternative exemplary implementation could prompt the user to turn off the breathing pattern after a period of time has occurred. Other breathing rates and rhythms may be used as well.

The device returns the user to the regular display after the breathing guide has been completed. The user then adjusts his breathing in the manner previously described to reduce the wave frequency down to 6, maintain rhythmic breathing, and increase the size of the waves by breathing more deeply. The user continues this process until the session timer reaches 0:00, at which time the session summary screen may be displayed (FIG. 29).

Several aspects of the present invention can be combined together to create a number of alternative exemplary embodiments. For example, the device can feature a meter that could be used as an amplitude feedback meter rather than a stress meter. The meter could further have a target bar. Thus, the device could graphically display how deeply a person is breathing so he could learn to take deeper breaths. If a target bar is used, users could try to breathe deeply enough with each breath to cause the meter to rise above the target bar. Any numerical or graphical feedback (visual or otherwise) of amplitude would be within the scope of this alternative embodiment.

Another alternative exemplary embodiment could use the wave information (e.g., wavelength, amplitude, and peak placement) to determine and provide feedback regarding the degree to which a user is following a prescribed breathing protocol (e.g., 6 breaths per minute with an inhale:exhale ratio of 1:3). Alternatively, the user could be given a breathing guide while being provided simultaneous auditory or visual feedback on how closely they are conforming to the guided breathing pattern. Furthermore, a target level could be displayed such that a user would be considered compliant if he were above the target level and non-compliant with the breathing protocol if he or she were below the level.

Alternative exemplary embodiments can use the variance of one or more wave parameters to detect rhythmic breathing. Then, the degree of rhythmic breathing can be visually displayed numerically, graphically, or in some other manner. Optionally, audible feedback may be provided. For example, in an exemplary embodiment a tone can increase as the breathing becomes more arrhythmic and decrease as it became more rhythmic. Alternatively, a single beep can indicate rhythmic breathing, a double beep can indicate near rhythmic breathing, and a triple beep could indicate arrhythmic breathing. Naturally, any of the previously mentioned feedback techniques or derivatives of these techniques could be used independently, in combination with each other, in combination with other techniques, or in combination with both each other and other techniques. Such an implementation may be used to practice yoga style rhythmic breathing patterns. For example, if the yoga student were practicing rhythmic breathing at an inhale:hold:exhale ratio of 1:1:1, he or she could use the device to ensure that rhythmic breathing was being maintained.

In other embodiments of the present invention, a pre-programmed breathing guide can be provided on the device so the user could follow the breathing guide while receiving visual and/or auditory feedback on the rhythmicity of his breathing. Furthermore, the breathing guide could be programmable. Optionally, feedback can be provided not only on the rhythm of the breathing, but rate as well. For example, if the user wanted to practice breathing at a 1:1:1 ratio at 5 breaths per second, visual and/or auditory feedback can indicate the degree to which a user is breathing rhythmically at five breaths per minute. Breathing at another frequency and/or arrhythmically would reduce the score.

Another exemplary embodiment provides feedback on the depth of breathing. During rhythmic breathing, a measurable phenomenon using aforementioned methods, the primary difference in wave amplitudes is the tidal volume (the depth of breathing). Thus amplitude measurements could be used for visual and/or auditory feedback to indicate the depth of a person's breathing. As stated previously, deep breathing is a useful way of relieving stress. Exemplary embodiments can provide feedback on a user's depth of breathing to assist teaching the user how to breathe deeply and to thereby relieve stress.

In short, exemplary embodiments of the present invention can provide auditory and/or visual feedback for the following: rate of breathing, rhythmicity of breathing, depth of breathing, breathing conformance to a prescribed rate/rhythm, and the like. An assessment can be made of each of these, alone or in any combination. Feedback can be provided on one or more of such assessments. Any implementation that identifies two or more RSA waves and derives rate, rhythm, depth, and/or conformance is within the scope of the present invention.

Exemplary Form Factor

Exemplary embodiments of the present invention incorporate a number of additional features. One such feature is the design of the device form factor. Prior to the present invention, biofeedback programs used finger PPG sensors, ear PPG sensors, and/or heart rate ECG sensors that attached to a computer via a wire. Although PPG sensors are sensitive to movement and finger pressure, the prior art did not have to deal with the many artifacts created by movement or excessive pressure because the prior art finger PPG sensors were often placed on tables or desks. In this situation, users could rest their hands and fingers on the desk which stabilized the hand and finger, thereby preventing excessive movement and finger pressure.

Since external wires are generally socially (and otherwise) unacceptable, an exemplary embodiment of the present invention integrates a PPG sensor directly into a portable device and eliminates external wires. As a result, devices according to exemplary embodiments of the present invention can be comfortably used in a public setting. Integrating a PPG sensor into a portable device, however, requires an innovative form factor. For example, since session times can range from 5-15 minutes, users of the device will be holding the device, without a stabilizing structure like a desk, for an extended period of time. Accordingly, the present invention provides devices which can be comfortably gripped, while simultaneously allowing the user to gently rest his finger on the finger sensor.

Figure 30:
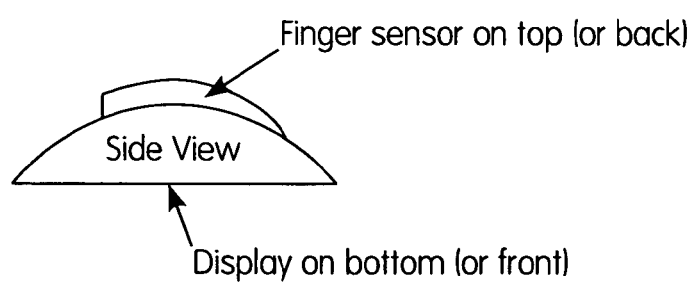
FIG. 30 illustrates an alternate form factor for exemplary devices of the present invention.

The present invention also provides form factors that provide comfort while minimizing artifacts caused by movement and pressure over extended periods of time (e.g., 10-15 minutes). Two exemplary form factors accomplish these objectives. In the first, the finger sensor is on the top of the device near one of the edges. Ergonomically, the height from the bottom of the device to the top may be between about 1.5 inches and about 3.5 inches and is preferably around 2.5 inches. This allows the device to be supported either by the thumb when held vertically (FIG. 15a), or supported by the curled fingers when tilted (FIG. 15b). In the second, the finger sensor is located on the rounded back of the device with the display on the front, allowing the device to rest, for example, in the palm of the hand during use (FIG. 30). The particularly preferred form factor is the first-described above which allows for the design of products with a scientific and medical look and feel.

Error Detection and Correction

While either form factor described above will minimize artifacts, the hardware form factor may not eliminate every possible artifact. Because there is no supporting structure such as a table or desk, the hand and finger will move at different times throughout the session. While the hardware will minimize artifacts, the remaining artifacts can be addressed by software in exemplary embodiments of the present invention. Also, the device not only detects when an error has occurred, but it also corrects the error.

Figure 31A:
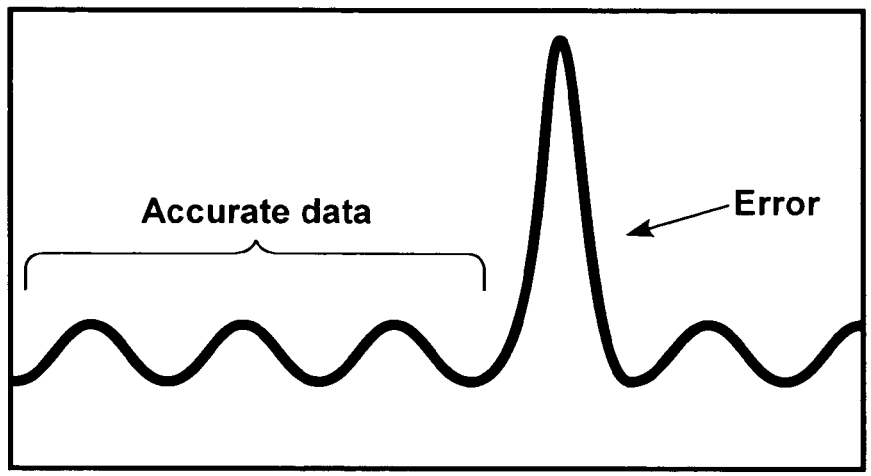
FIG. 31a-b illustrate, respectively, a display having sufficient size to show both accurate data and erroneous data and a display of a small, portable device in which only the erroneous data is discernable.
Figure 31B:
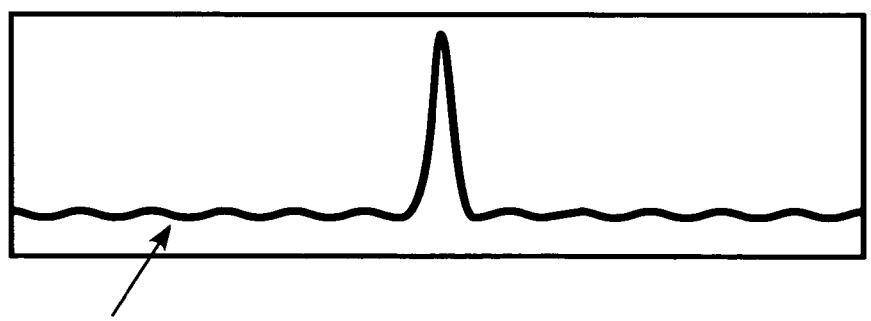

In general, displays on small portable devices are much more sensitive to errors because such displays are very small compared to that of a desktop computer, for example. When an error occurs on a desktop computer, the display has enough resolution to show both the accurate data and the error (FIG. 31a). On a small, portable device, however, one error can cause all the correct data to become indiscernible due to its low resolution (FIG. 31b).

Numerous statistical methods for detecting errors in a data stream exist in the state of the art. However, these methods require a large sampling of data before they provide a high degree of accuracy. As mentioned above, devices having small displays can be adversely affected by even a single error. Thus, errors should be detected quickly and accurately and then corrected. Devices according to an exemplary embodiment of the present invention implement a novel method of error detection and correction that requires only a small amount of data (approximately 10 seconds) before it becomes highly accurate.

Figure 32:
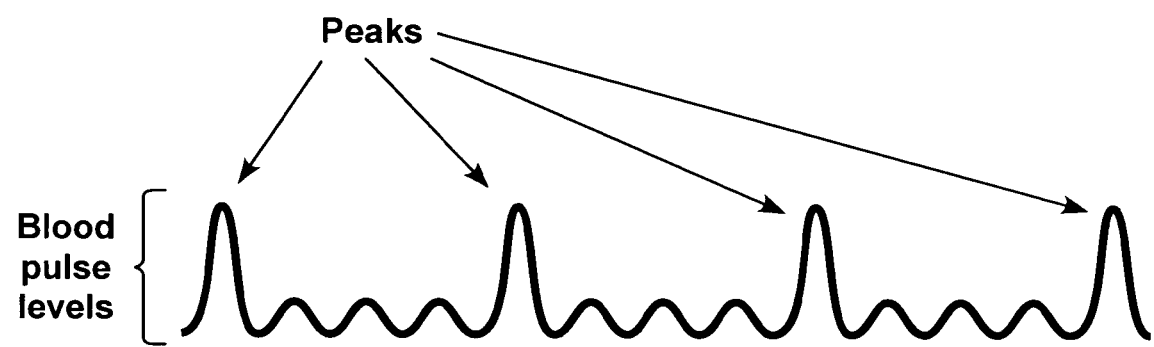
FIG. 32 illustrates a series of representative pulse peaks.

To facilitate further understanding of the error detection and correction methods of the present invention a brief explanation of how PPG sensors are used to obtain pulse information in ideal, error-free conditions is provided. PPG sensors detect the amount of blood pressure in the finger on a continual basis. Each time the heart beats, the corresponding pulse of blood results in a rapid increase in blood pressure in the finger, which then quickly subsides. The PPG sensor continually seeks to identify the time when the blood pressure peaks (FIG. 32). This is the pulse peak. As discussed previously, the amount of time (in milliseconds) between two consecutive pulse peaks is called the pp interval (pp) (FIG. 2). Devices according to the present invention can record each successive pp interval. The pulse rate of each recorded pp interval (60,000/pp) can be displayed on the screen each time a new pulse peak is encountered. The absolute time difference between successive pp intervals (absolute (pp[n]−pp[n−1])) is called the interbeat interval time or IBI (FIG. 3).

Figure 33A:
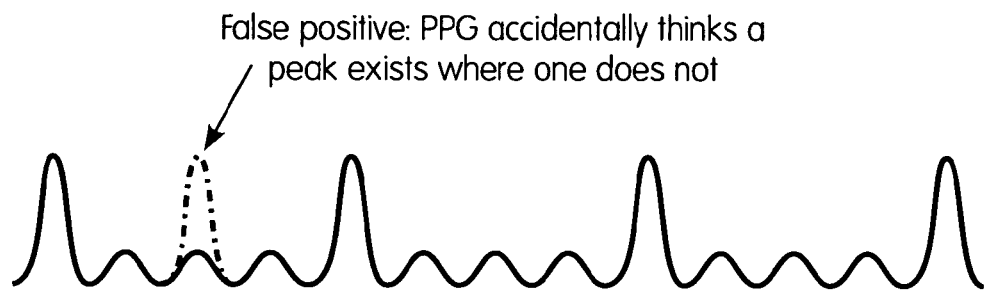
FIG. 33a-b illustrate, respectively, a representative false positive pulse peak and a representative false negative pulse peak.
Figure 33B:
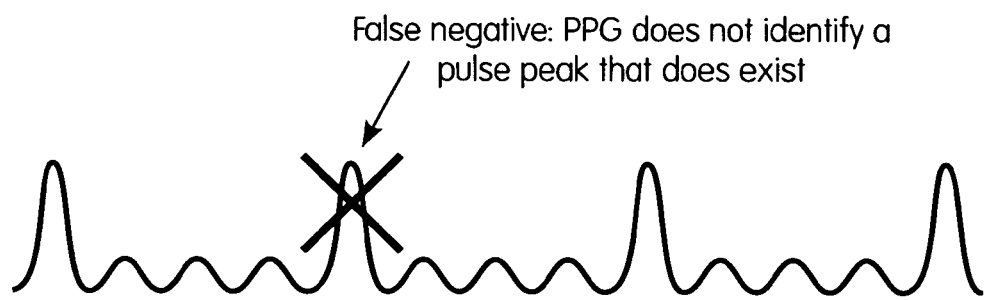

Two types of errors occur when the PPG sensor is attempting to correctly identify the next pulse peak. (FIG. 33) One type of error can occur when the PPG sensor incorrectly identifies an artifact as a pulse peak. That is, the PPG sensor determines that a pulse peak occurs where one does not actually exist. This type of error is called a false positive error. The second type of error occurs when the PPG sensor does not identify a pulse peak that does exist. This is called a false negative error. Both false negatives and false positives result in large IBIs Error free data may or may not result in large IBIs. However, erroneous data always produces a large IBI. Thus, wherever there is an extended amount of consecutive data that does not contain a large IBI, one can safely assume that this data is free of errors. Where large IBIs occur, it may be due to an error or may be good data; the device will need to determine which is the case.

According to preferred exemplary embodiments of the present invention, the first step in the error detection strategy is to wait for a certain number of heart rate related intervals (e.g., 10 pp intervals) where every IBI time is less than 200 ms. These data points are considered to be error free. The number of consecutive intervals can be less than 10 but needs to be at least 2, preferably at least 3 and even more preferably at least 5. Another alternative is to wait for a set of consecutive data points where every IBI time is less than ⅓ of the lowest heart rate related interval, such as a pp interval, in the consecutive data set (e.g., 5 consecutive pp intervals). The range of these data points can be computed. As used herein, "range"

can refer to the absolute range (i.e., min pp to max pp), a derivation of the range (e.g. ((min pp−10%)−(max pp+10%)), or as a computed variation (e.g. mean deviation, standard deviation, etc.). Any appropriate mathematical description of the range can be used. Preferred embodiments according to the present invention use min pp−((max pp−min pp)×25%) as the bottom of the range. The preferred embodiment uses max pp+((max pp−min pp)×25%) as the top of the range. The range may be derived from the entire data set or a subset of the data set.

Once the range has been established, each new p-p is tested to determine if it is "in range". In exemplary embodiments, a new pp value is considered "in range" if it is greater than the bottom value and less than the top value. However, "in range" also can refer to any mathematical determination of close proximity of the current p-p to the range as determined by the selected range calculation. For example, if the range was calculated using the standard deviation, "in range" could refer to the statistical determination that the current p-p has an 80% or higher probability of being within the computed variation.

As new pp intervals arrive, the new IBI also may be computed (absolute new pp−previous pp). The new IBI may be tested to determine if it is "large". In preferred embodiments, the device tests whether the IBI is greater than one half the bottom value of the range. If it is greater, the IBI is considered to be large. In other exemplary embodiments, the IBI time of the new pp interval minus the previous interval can be computed. Other IBI times could be used instead, such as the IBI of the new p-p compared to the average p-p of the last n number of pp intervals. Also, different implementations can use a different threshold for distinguishing large IBIs from non-large IBIs. According to embodiments of the present invention, any implementation can be used that uses the difference of pp intervals or the difference of a derivative of pp intervals (such as the average) in order to detect an error.

To summarize the above, when the device according to exemplary embodiments of the present invention begins, it may not enter error detection mode until 10 consecutive pp intervals are located where all the IBI times are less than 200 ms. Then, the device can calculate the range of these pp intervals and initiates an error detection mode. In the error detection mode, the device can test each new pp to determine if it is "in range" and the device tests each new IBI to determine if it is "large". Any other suitable method of determining either or both of these two properties for use in error detection also is within the scope of the present invention.

If the next p-p is "in range" and the IBI is not "large", then the new p-p can be considered to be error-free. If the p-p is not "in range" and the IBI is not "large", the new p-p can be considered to be error-free and the range is recalculated to include the newly found pp value. If the new p-p is "in range" but the IBI is "large", the new p-p can be considered to be error-free. However, when the new p-p is "out of range" and the IBI is "large", then the new p-p can be considered to be the result of an error. Once an error has been detected, it should be corrected. Therefore, each time that an error is detected in error detection mode, the device changes to error correction mode. The device can remain in error correction mode until erroneous condition has been resolved.

Figure 34:
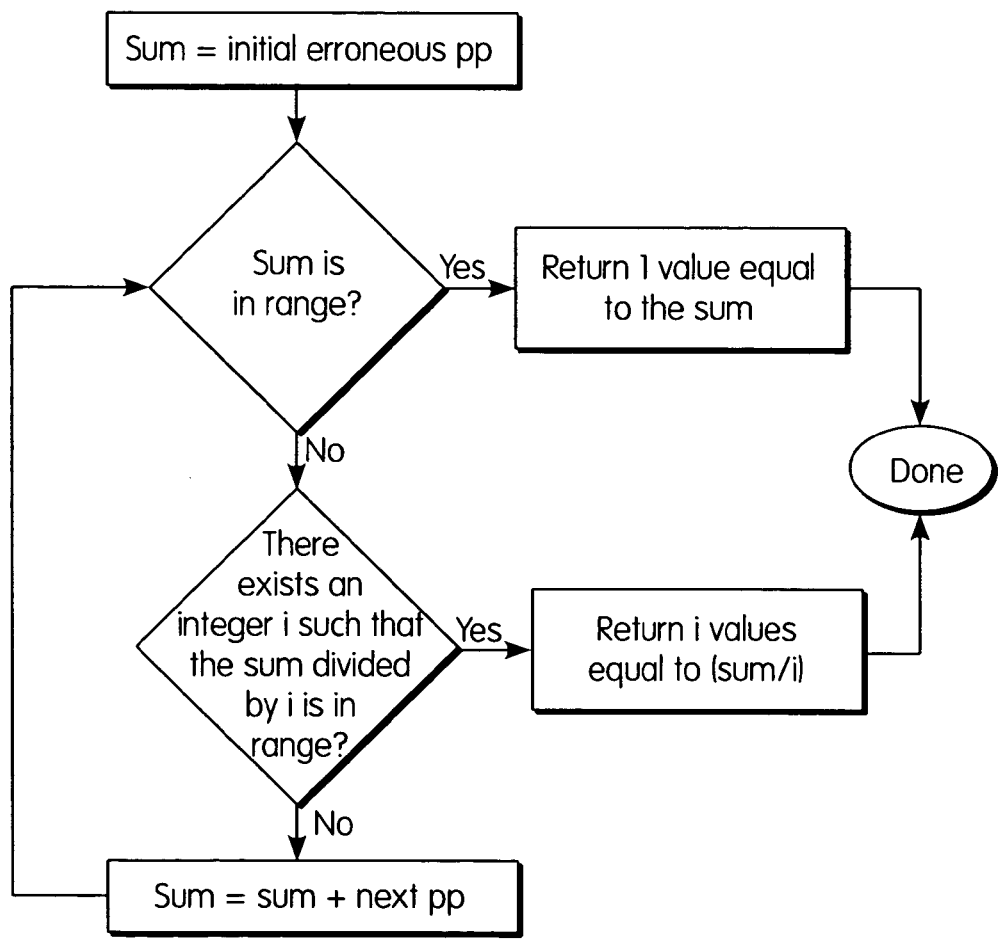
FIG. 34 depicts an exemplary process flow for an exemplary error correction method employed during a representative error correction mode.

FIG. 34 provides a flowchart showing an exemplary error correction methodology employed during an error correction mode. Error correction includes summing together each successive pp interval as it is identified until either the sum of the pp intervals is "in range" or the sum can be divided by an integer such that the result of the division is "in range". When the sum itself is "in range", all the pp intervals forming the sum can be combined together into a single value equal to the sum. When the sum divided by an integer is in range, the erroneous values can be replaced with n (where n=the integer denominator) number of values equal to the result of the division.

The following discussion provides examples of how errors may be corrected according to an exemplary embodiment of the present invention. For example, if the range is 600 ms-1,000 ms, and the erroneous pp interval time is 200 ms. The next pp interval is 100 ms. The sum is now 300 ms. It is not "in range". The next pp interval is 400 ms. Therefore the sum is now 700 ms. It is "in range" and therefore 700 ms is the corrected value. The three pp intervals (200 ms, 100 ms, and 400 ms) will be combined into one value of 700 ms. The device then returns to error detection mode.

As another example, if the range is 700 ms-1,000 ms, and the erroneous pp interval is 1,300 ms. There are no integers which one can divide 1,300 ms by that will result in a value "in range". Therefore, the next pp interval (300 ms) is summed together to produce 1,600 ms. At this time, there is an integer which can be used in a division to produce a value "in range". The integer 2 results in a value that is "in range" (1600/2=800 ms). Therefore, the two erroneous values (1,300 ms and 300 ms) will be replaced with two (the integer number) values of 800 ms (the result of the division).

In exemplary embodiments, devices according to the present invention will be able to generate corrected values within one or two additional pp intervals. However, it is possible that a device may enter error correction mode indefinitely. Therefore, the present invention can include a safety mechanism to resolve this situation if it should occur. For example, if the device remains in error correction mode for too long, then the device recalculates the range by applying a statistical method to all original data points encountered. That is, every unprocessed pp interval received from the PPG sensor is used. The range is then computed with a statistical based range calculation, for example, a standard deviation formula. In exemplary embodiments, the median pp interval is determined from all unprocessed pp intervals encountered (whether authentic or erroneous). The range is defined as 15 beats per minute below the median up to 15 beats per minute above the median. The pp intervals in the error queue are reprocessed according to the new range. Note that the range could also be computed with a subset of the unprocessed data points (e.g., the last 50 data points). The present invention also can include any method of recalculating the range to resolve an extended error condition.

As stated previously, PPG sensors are sensitive to movement and finger pressure. They are also sensitive to bright light and cold fingers. Therefore, there are a number of factors that can cause multiple errors. In certain embodiments of the present invention, whenever the signal to noise ratio over ten seconds drops below 25%, the device may cycle a display of error messages (such as that shown in FIG. 18) until the device exits from error correction mode. Thus, the user will be provided information on changes can be made to assist the device in gathering accurate pulse information.

The present invention also provides alternative methods for detecting and correcting errors in a heart rate interval data set. For example, there are a number of implementations that would permit the range and/or IBI thresholds to dynamically change as new heart rate interval values were detected. Such implementations may provide a marginal increase in accuracy in certain circumstances.

For example, the range may be continually assessed using a rolling window. The range may be initialized after receiving the first 10 seconds of pp intervals such that each consecutive IBI is less than 200 ms. After this point, the range could be continually reassessed using a rolling window of the last 10 seconds of reliable data. The last 10 seconds of reliable data may or may not be consecutive. For example, the top of the range (r_top) could be the highest p-p in the last 10 seconds of reliable data and the bottom of the range (r_bottom) could be the lowest p-p in the last 10 seconds of reliable data.

Another alternative is to dampen the rate in which the range can dynamically expand and contract. For example, each time a new pp value is detected, the range could be updated in three steps. First the data set top (ds_top) and the data set bottom (ds_bottom) are identified from the last 10 seconds of reliable data. Second, the ds_top and ds_bottom are adjusted in a manner such that they do not change significantly from the previous ds_top (p_ds_top) and the previous ds_bottom (p_ds_bottom). For example, if the p_ds_top is greater than ds_top, then ds_top could be reset to p_ds_top−((p_ds_top−ds_top)/25+1). If p_ds_top less than ds_top then ds_top could be reset to p_ds_top+((ds_top−p_ds_top)/4+1). If p_ds_bottom is greater than ds_bottom then ds_bottom could be reset to p_ds_bottom−((p_ds_bottom−ds_bottom)/2+1). If p_ds_bottom is less than ds_bottom then ds_bottom can be reset to ((ds_bottom p_ds_bottom)/25+1). Thus, r_top would be equal to the adjusted ds_top and r_bottom would be equal to the adjusted ds_bottom. A p-p would be considered "in range" if it is between r_bottom and r_top.

The above-described methodology can accomplish three objectives. First, it allows the range to dynamically increase and decrease. Secondly, the range can expand faster than it contracts. Third, the bottom of the range can expand faster than the top of the range. There are a number of ways to implement these methods and any implementation that accomplishes any of these three objectives is intended to be within the scope of the present invention.

Yet another alternative includes converting the computed pp range to a range of pulse rate values (prv) and comparing each newly detected prv (60,000/pp) to the pulse rate range. "In range" could be determined by whether or not the new prv was less than the maximum prv (max_prv) and greater than the minimum prv (min_prv). Or, "in range" could refer to whether or not the new prv was sufficiently close to the range of prv values. For example, the range top and range bottom could be expanded by a determined number of beats (i.e. max_prv=max_prv+9 and min_prv=min_prv−9). Thus, any new prv that is within 9 bpm of the data set range could be considered 'in range'.

As with pp ranges, prv range calculations can also be dynamic. That is, as new prv's arrive, the range could be recalculated if the new prv is considered to be reliable (e.g., IBI is not too large).

Another method for increasing error detection capabilities is to use two threshold values for determining how close a new IBI is from the previous IBI. For example, if the new IBI is less than the low threshold, it can be considered a "small jump". If the new IBI is between the two thresholds, it can be considered a "significant jump". And if the new IBI is higher then the second threshold, it can be considered a "large jump". Thus, as new values come in, they could be assessed as to whether the new value is "in range" or "out of range", and whether the new IBI is a small jump, significant jump, or large jump. Decisions on whether to display the value, use the value for updating the range, and/or whether to correct the value may be based upon such assessments.

Any heart rate related interval may be used for determining the significance of IBI levels. For example, the inter-beat interval difference of two prvs (the prv IBI) could be used when assessing the proximity of the new pulse value to the previous pulse values. Thus, IBI's can be computed and assessed for pp intervals, prv values, rr intervals, hr values and the like.

Still another alternative includes using the direction of the IBI change to determine whether the jump is small, significant, or large. When a person is physically still, pulse rates can rise or fall at different rates. Thus, different thresholds could be used depending on the direction of the change. For example, a prv IBI that's greater than the previous prv IBI could be considered to be a small jump up if it is less than 8 bpm, a significant jump up if it is between 8-15 bpm, and a large jump up if it is greater than 15 bpm. And a prv IBI that's smaller than the previous prv IBI could be considered a small jump if it is less than 8 bpm, a significant jump if it is between 8-12 bpm, and a large jump if it is greater than 12 bpm.

Yet another exemplary embodiment includes basing the prv IBI thresholds on the location of the previous prv in the range. If the previous prv is already toward the top of the range, the threshold could be set smaller, since in theory, one would not want the next pry to jump too far outside the range. Likewise, if the previous prv is already toward the bottom of the range, the prv thresholds for jumping down could be decreased. Thus, examples of prv IBI thresholds based on the location of the previous prv in the range could include: ((r_top−prev_prv)(⅓))+10 for a small jump up, ((r_top−prev_pr)(⅔))+15 for a large jump up, ((prev_prv−r_bottom)(½))+10 for a small jump down, and ((prev_prv−r_bottom)×(⅔))+15 for a large jump down.

Yet another exemplary embodiment is to add a third test such as direction when determining if a new heart rate interval point needs to be corrected. For example, if the point fails the IBI and the range tests, but is closer to the range then the previous heart rate interval point, then it could still be considered acceptable.

In certain circumstances and implementations, a marginal improvement may be obtainable by combining the dynamic range method, the double IBI threshold method with different thresholds based upon direction, and the heart rate interval direction method. An example of such a combination is as follows. As each new prv is calculated (60,000/pp), it can first be assessed whether or not it is 'immediately displayable'. If the prv is a small jump up or small jump down (using appropriate thresholds) it is 'immediately displayable' and therefore is immediately displayed. If it is a significant jump but is 'in range' then it is 'immediately displayable' and therefore is immediately displayed. Otherwise, it could be re-evaluated by direction to see if it is displayable. If the current prv is closer to the range than the previous prv, then it is still displayed. Otherwise, it is not displayed and must be corrected.

Combinations of the above-described methods also may be used to determine when a value was 'reliable' or not. That is, these methods may be used to determine whether a new prv should be used in recalculating the dynamic range. For example, if the new prv is a small jump, it could be considered 'reliable'. If the new prv is a significant jump, but is 'in range' then it could be considered 'reliable'. And if the new prv is a significant jump and 'out of range' but is closer to the range than the previous prv, then it can be considered 'reliable'.

In deciding which methods to employ to detect and correct errors in a data set, one should consider the hardware stability, use environment, and other factors to determine if the degree of potential statistical advantage of complex combinatorial methods offers a greater practical utility over the basic IBI/range methodology. In most situations the basic IBI/range strategy is quite sufficient. If, however, significant movement, sunlight, pressure and similar factors are expected to be present, the additional statistical methodology described above may be implemented to provide even greater accuracy in detection and correction of errors in a data set.

Resolution of Scaling Problems and Identification of Rhythmic Breathing

Methods and devices according to exemplary embodiments of present invention not only use wave information to assess stress, determine an accurate average heart rate, and provide feedback on the wave frequency, but also use the wave information to innovatively scale the area of the display where the waves are shown.

The amplitude of RSA waves can vary significantly from person to person. As described earlier, RSA amplitude depends on the individual's age, sex, fitness level, breathing pattern, and more. While large display screens can accommodate large waves or small waves, small display screens on portable devices require sophisticated scaling. Thus, if the scale on a small display is too small, then large waves will not fit on the display. If the scale is too large, then the shape and size of small waves will become indiscernible. And if the scale is too dynamic and adjusts too frequently, then large waves and small waves will appear to be the same size, and the user will not be able to discern whether or when his breathing pattern has changed.

Devices according to the exemplary embodiments of the present invention can solve the scaling issue by adjusting the display scaling differently during two stages. The first stage lasts from the time the device is powered on until the user begins to breathe rhythmically. The second stage lasts from the time the device detects rhythmic breathing until the device is turned off. During stage 1, a very basic scaling technique can be implemented. During stage 2, an innovative approach can be employed so the user can accurately assess when his breathing has become more shallow (less deep).

For example, when the device is first turned on, the scaling is preferably zoomed in to a small, preset value. Then, the device zooms out whenever a pulse rate point is encountered that is greater than highest value or lesser than the lowest value that can be plotted using the current zoom level. The scale is zoomed out such that the new pulse point is plotted at the edge of the device display area. To give the user an idea of scale, the device only zooms out, not in, at the beginning. The display also zooms back in after large waves have exited the screen, so that the full height of the display is used from top to bottom. The display continually zooms in and out such that the data points being shown consume the full range of the display at all times until the user begins rhythmic breathing.

Once the user begins to breathe rhythmically, the device seeks to encourage him to breathe deeply. If the device continued to automatically zoom in when small waves appear, then the small waves produced by shallow breathing will appear the same size as the large waves produced by deep breathing. This will not allow a user to visually discern his depth of breathing from the size of the waves.

Figure 35:
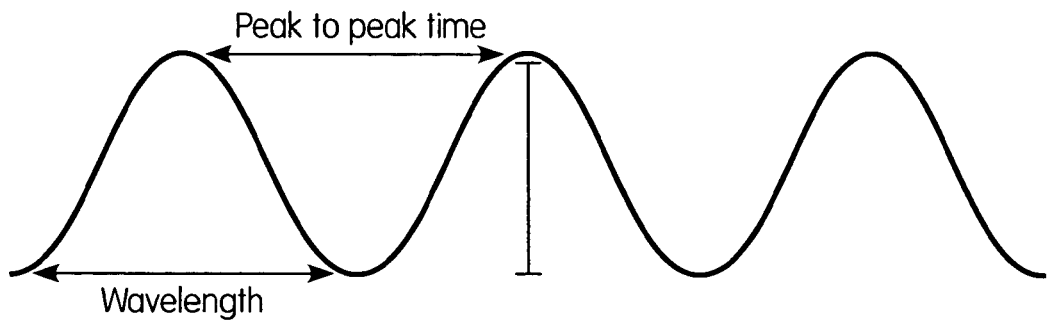
FIG. 35 illustrates representative wave features which may be used to determine when a subject has achieved rhythmic breathing.

Devices according to exemplary embodiments of the present invention use the wave information to detect rhythmic breathing. Rhythmic breaths produce waves with uniform wavelengths, frequencies, amplitudes, peak to peak times, and peak placement times (FIG. 35). By measuring the variance of one or more of these wave feature parameters, rhythmic breathing can be identified. Exemplary embodiments calculate the variation of the wavelengths and amplitudes of the last three waves. When both of these variations are low, then rhythmic breathing is considered to have begun.

One method of determining variance, and thus establishing when a variance is small, can be based on the percent relative deviation. This method is useful when comparing the variation of two or more values (e.g., peak-to-peak times, wavelengths, frequencies, etc.). This may be done as described below. First the mean (average) of the values can be determined. Then the sum of the difference (sum_dif) of each value from the average can be computed. The sum can be divided by the average×number of values. For example, consider four wavelengths: 10, 8, 10, 8 seconds. The average is 9. The sum of the differences from the mean is 4 (10 is 1 away, plus 8 is 1 away, plus 10 is 1 away, plus 8 is 1 away). Thus 4 is divided by the mean×number of values (4/(9×4)). Thus the percent relative mean deviation is 11.1%. Consider four amplitudes: 30, 28, 30, 28 bpm. Although the deviation is also 4 as in the previous example, the percent relative mean deviation is only 3.4%. Thus, percent relative mean deviation automatically scales itself to the range of the values being analyzed.

The variance of any of the wave features can be analyzed alone or in combination using numerous methods. The preferred embodiment employees percent relative mean deviation. The greater the resulting percentage, the greater the variance. A variance threshold could be set to determine if rhythmic breathing has commenced. For example, if three or more waves have a variation in a wave feature less than 20%, one may conclude that rhythmic breathing has commenced. In a preferred embodiment, rhythmic breathing is considered to have commenced when the variation of the wavelength and amplitude of the last three waves is less than 10% each.

Once rhythmic breathing has begun, the can keep track of the largest amplitude (maximum amplitude) formed by the resulting rhythmic waves. The device continues to determine if the user is still breathing rhythmically with, for example, each and every wave. As long as the user continues to breathe rhythmically, the device will continue to look for the largest amplitude (maximum amplitude). If a newly formed rhythmic wave has a higher amplitude than the current maximum amplitude, then the maximum amplitude can be readjusted to be equal to the new amplitude. In general, the display does not zoom in more than the maximum amplitude. That is, the display scale can be set such that a wave with an amplitude equal to the max amplitude would fully consume the screen from top to bottom. The zoom level can be set to not exceed this set point. As a result, the device can zoom out, but it may not zoom in beyond the set point determined by the maximum amplitude. In this way, users will notice when they are breathing shallowly, because they will see the relatively smaller waves (relative to the maximum amplitude) on the screen.

Sometimes an erroneous wave (a wave with corrected errors that is incorrectly reconstructed) can have the largest amplitude. This large amplitude may be erroneously high. Also, a person's largest possible amplitude can degrade with time until their lungs become used to rhythmic breathing. That is, as their lungs become tired, they will not be able to reproduce waves with amplitudes equal to the maximum amplitude. Since the device should not frustrate the user, but rather encourage him to produce the largest waves that he comfortably can, the device can decrease the maximum amplitude value over time if a successive series of waves do not come sufficiently close to the maximum amplitude. In preferred embodiments, if three consecutive rhythmic waves have amplitudes less than 80% of the max amplitude, the maximum amplitude may be readjusted using the following formula: (largest amplitude of the last three waves)×(100/85). Another alternative is to continually decrease the maximum amplitude until the waves are sufficiently close to occupying the display from top to bottom. For example, the maximum amplitude could be decremented by 5% every time a newly formed rhythmic wave has an amplitude less than 80% of the current max amplitude. Another way to use amplitudes would be to take the highest average amplitude. For example, the average amplitude of the last three waves could be calculated every time a new wave is encountered. The highest average amplitude can be used as the minimum set point.

The use of high amplitudes which occur in rhythmic breathing to establish set points is a novel and useful component of the disclosed invention. Any scaling based upon amplitude, range, variance, or deviation is intended to be within the scope of this invention. For example, the standard deviation of the data set, or subset of the data, could be determined. The maximum zoom level could be set such that values with a certain probability relative to the deviation consume the screen. For example, all values that have an 80% probability of being within the standard deviation would fill the screen from top to bottom.

Exemplary System and Software Process

Figure 55:
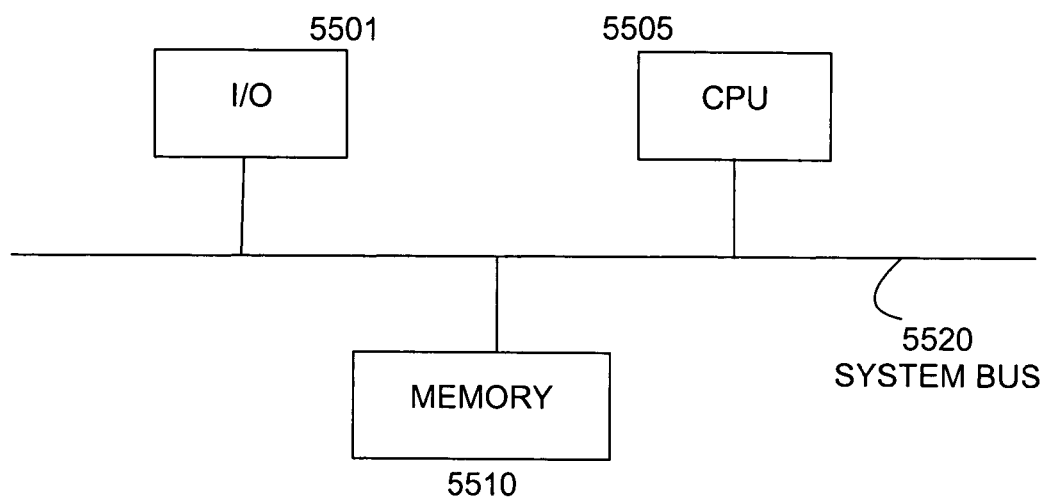
FIG. 55 depicts an exemplary system in which a software process can be implemented according to an exemplary embodiment of the present invention.

An exemplary embodiment of the present invention can be implemented, for example, as a process stored in a memory of a data processing device, such as, for example, a computer. Such a process, can, for example, be in the form of software, and can, for example, be executed by a data processor or CPU and the results displayed on a display, such as, for example, a CRT, plasma or other computer display as is known in the art. Thus, for example, such software can be implemented on a system comprising a CPU, a memory, and a display, all connected by one or more busses or data pathways. FIG. 55 depicts such an exemplary system.

With reference thereto, there is provided an I/O or input/output interface 5501, a CPU 5505 and a memory 5510. The three components of the exemplary system are communicably connected via a system bus 5520. As noted, system bus 5520 is a logical component, and in any given embodiment, can comprise a plurality of interconnections between system elements. Given such an exemplary system, a software process can be loaded in memory 5510 and executed in CPU 5505. Moreover a user can provide input to the process via the I/O 5501, and output to user by way of visual, auditory, tactile, or other means can be provided to a user also using the I/O. Such I/O can comprise a physical interface device, comprising one or more sensors, or can, for example, comprise one or more of a microphone and one or more speakers, a keyboard, mouse and visual display, and a tactile input and output mechanism.

Additionally, such a software process can, for example, be expressed using any appropriate computer language or combination of languages using known techniques, and can be, for example, implemented as an embedded system or a conventionally stored program of instructions using known techniques. Such a software process can be implemented, for example, on a device which can be used to evaluate stress in humans, as described above.

Such an exemplary software process can have, for example, a top level process that interacts with a user by displaying messages to a user and by, for example, continually looking for and responding to various user actions, such as, for example, a user pressing a breathing guidance button or a pulse emanating from a user's finger. Such an exemplary software process is depicted in FIGS. 36-54, as next described. It is noted that FIGS. 8(a)-(b), described above, integrate with this exemplary software process, and thus the "process_waves" subroutine, described below in connection with FIG. 49, calls the subroutine "get_waves" depicted in FIGS. 8(a)-(b).

Figure 36:
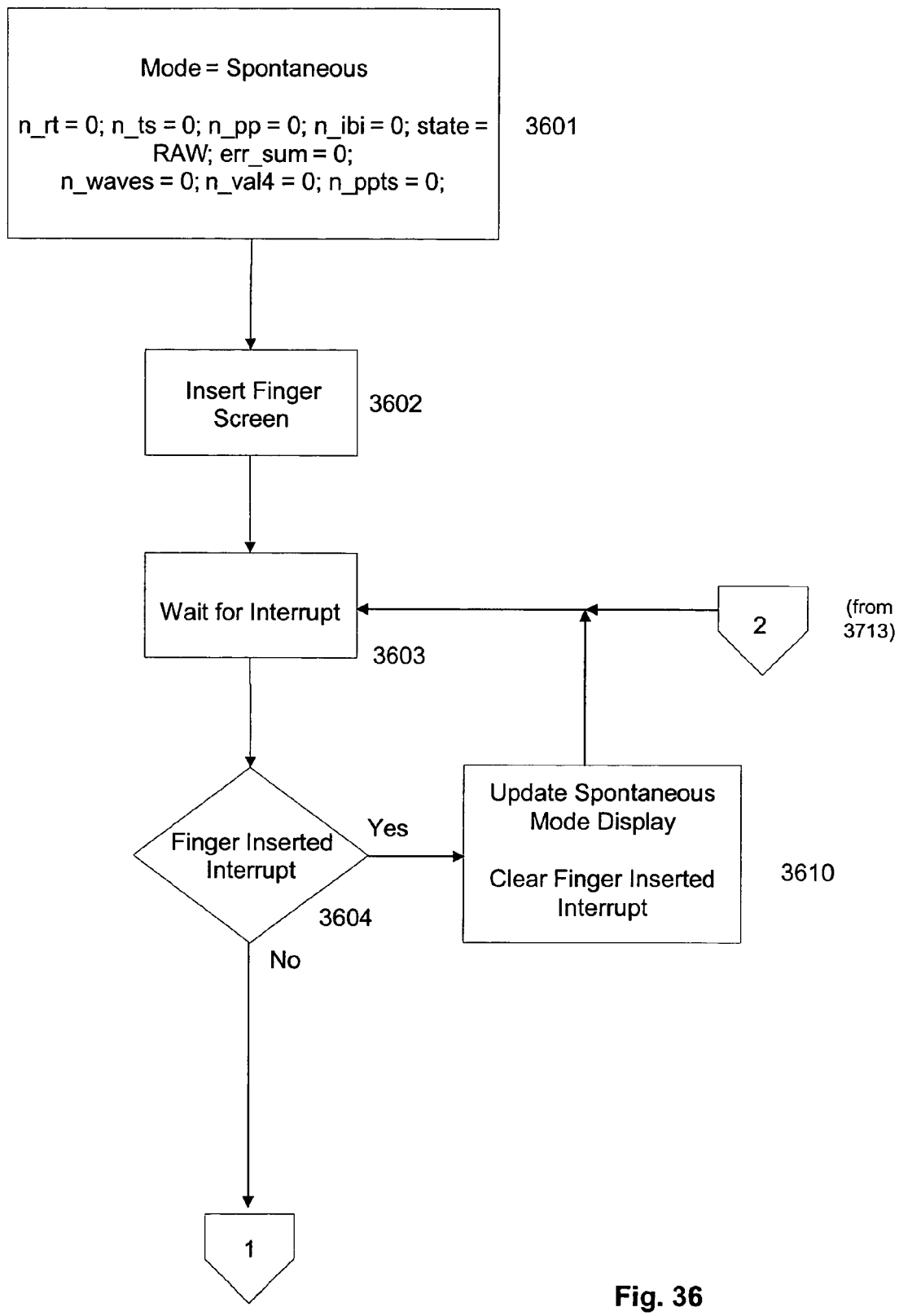
FIGS. 36-37 depict an exemplary process flow for an exemplary top level procedure for interacting with a user according to an exemplary embodiment of the present invention.

FIGS. 36-37 depict an exemplary top level process, which can control what is displayed to a user and can, for example, respond to user actions. This top level process essentially initializes variables and then waits for interrupts to which it responds. With reference to FIG. 36, at 3601 variables can be initialized. This initialization can include, for example, setting the device mode to "Spontaneous" and setting the values for the following variables to zero: number of raw timesteps, number of timesteps, number of pp intervals, number of interbeat intervals, error sum, number of waves, number of pp intervals and number of pp interval timesteps, as well as setting the variable state to RAW. This initialization can, for example, be implemented according to the following pseudocode: n_rt=0; n_ts=0; n_pp=0; n_ibi=0; state=RAW; err_sum=0; n_waves=0; n_val4=0; n_ppts=0.

Continuing with reference to FIG. 36, at 3602, for example, an "Insert Finger" message can be displayed to a user. At 3603, the process waits for an interrupt, taking no further action until one occurs. At 3604, if a finger is inserted by a user then at 3610, for example, the device begins calibration, the display message is updated and the interrupt cleared, returning to 3602. Process flow for this exemplary top level process continues as depicted in FIG. 37. With reference to FIG. 37, at 3710, if a user presses the breathe button, as described above, this can trigger a Breathe Button Pressed Interrupt. Process flow then moves to 3720, for example, where the device mode is set to "Guided", the variable Start set to be the current time and the interrupt cleared. Process flow can then move to 3721, where a clock interrupt can be, for example, set to 100 milliseconds. Process flow can then move to 3730, where the Guided Mode display can be presented to the user. Process flow then returns through breakpoint 2 in FIG. 37 back to 3603 of FIG. 36, where the top level process again waits for another interrupt to occur. This brings process flow back to FIG. 37 through breakpoint 1 where, at 3711, for example, if a clock interrupt occurs, process flow moves to 3703, and tests whether less than two minutes have elapsed from the time the user pressed the Breathe Button at 3710 and entered Guided Mode. If it is still less than two minutes, process flow can move through 3731 to 3730 where the Guided Mode display can be, for example, updated. If at 3703, for example, it has been longer than two minutes since the user pressed the Breathe Button, then process flow can move to 3702, the Mode variable is reset to "Spontaneous", and process flow moves to 3701 where, for example, the Spontaneous Mode display is restored.

Finally, with respect to FIG. 37, at 3712, if a pulse is detected, a Pulse Detected Interrupt occurs, and process flow moves, for example, to 3713, where the Process Pulse subroutine is called. This ends the exemplary top-level process depicted in FIGS. 36 and 37.

Figure 49:
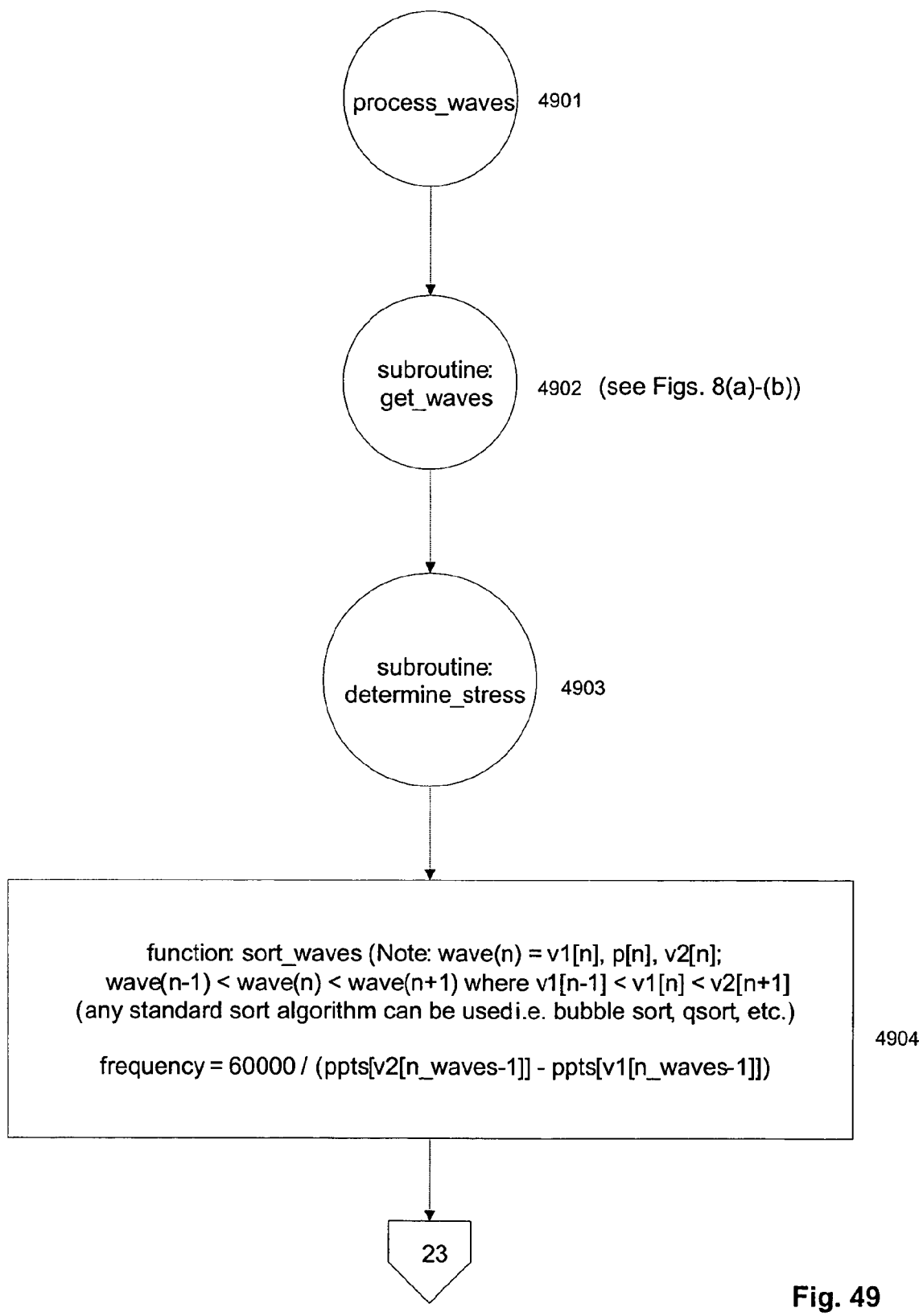
FIGS. 49-50 depict an exemplary process flow for an exemplary procedure for processing RSA waves within a sequence of detected pulses according to an exemplary embodiment of the present invention.
Figure 50:
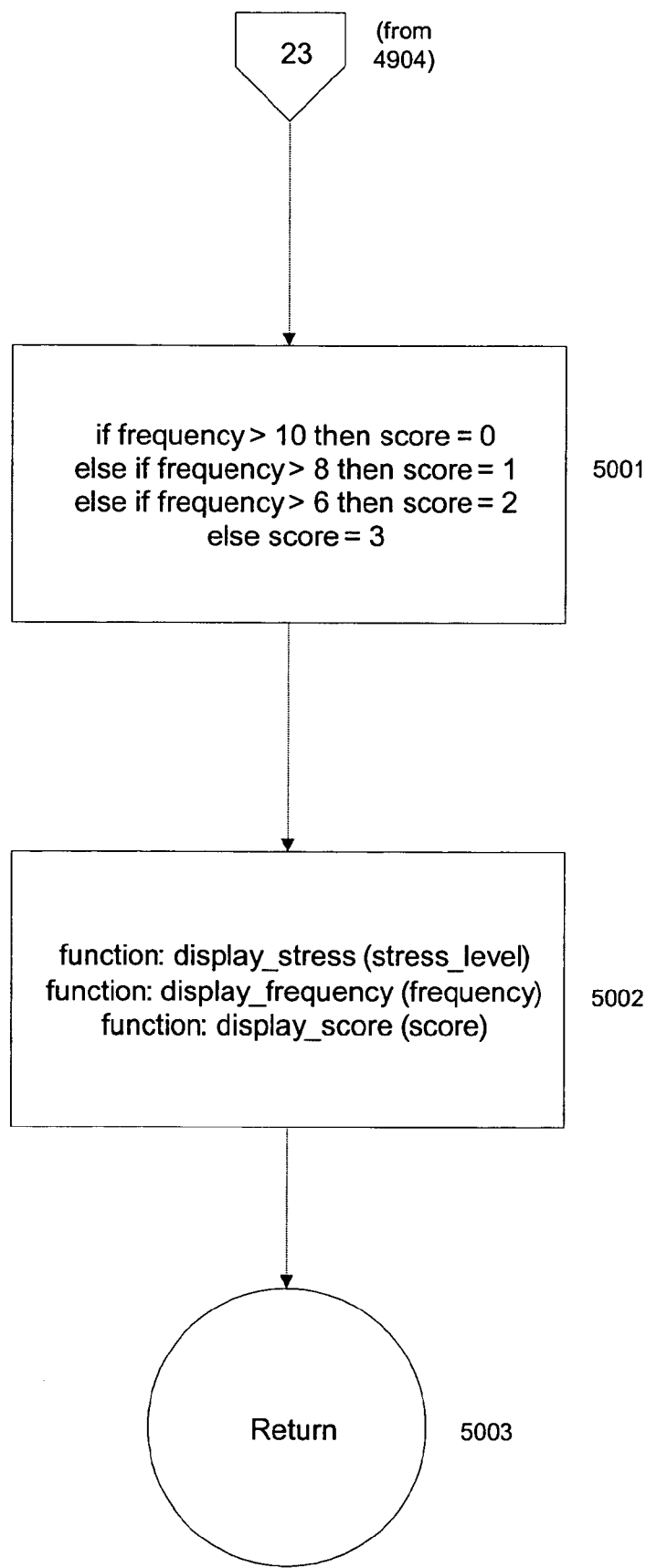
Figure 51:
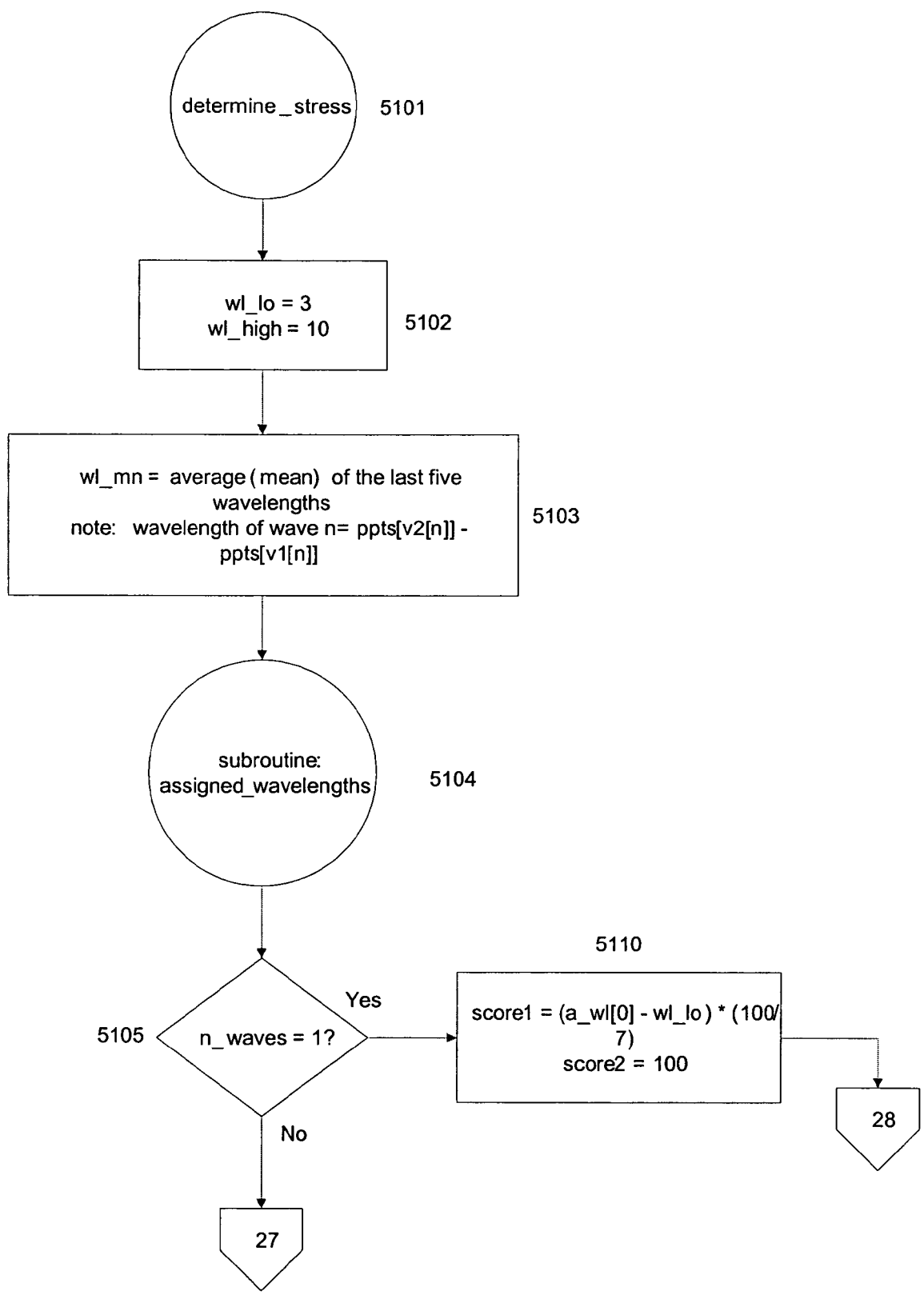
FIGS. 51-53 depict an exemplary process flow for an exemplary procedure for processing RSA wavelengths within a sequence of detected pulses to determine a stress level for a user according to an exemplary embodiment of the present invention.
Figure 52:
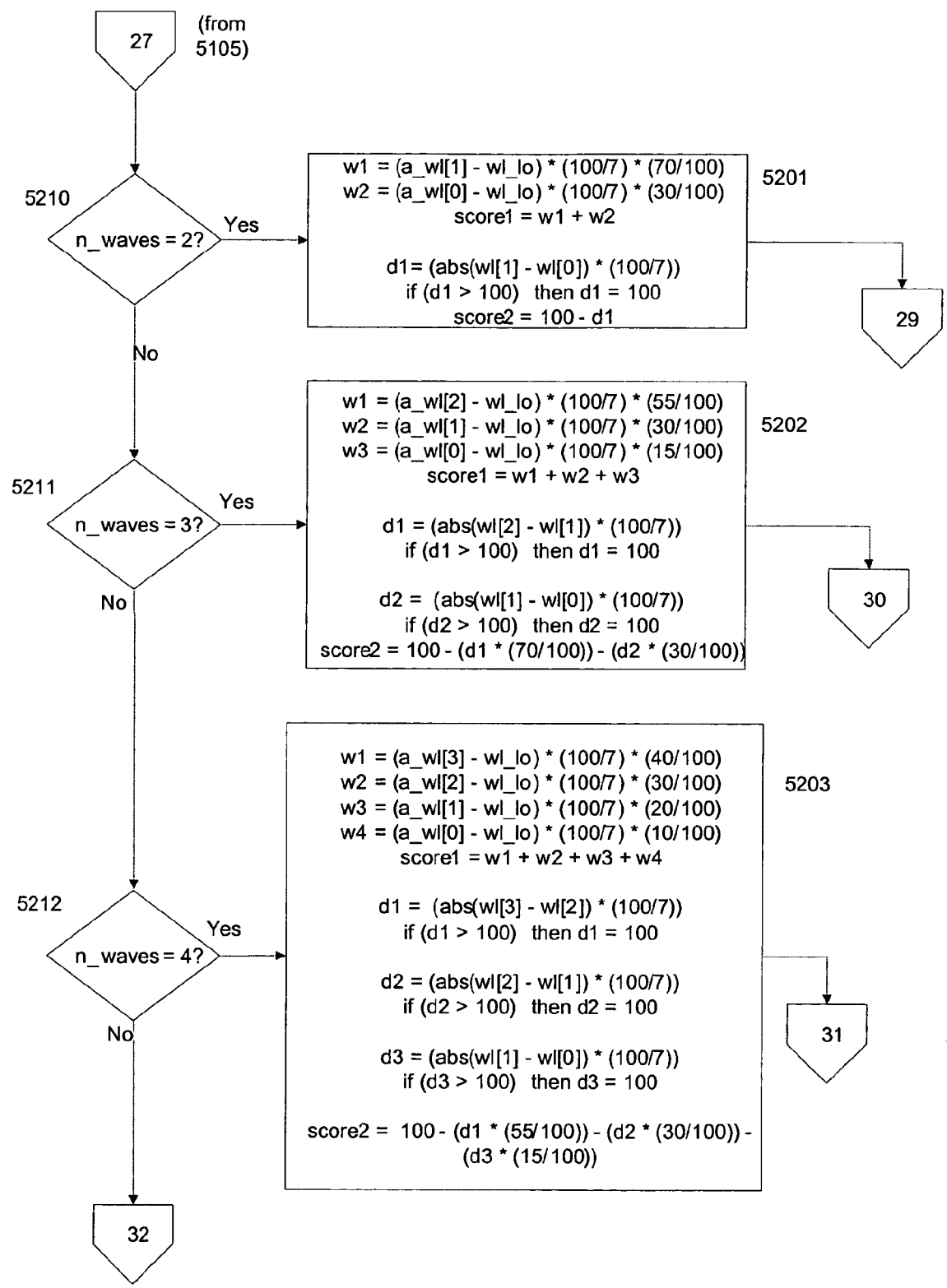
Figure 53:
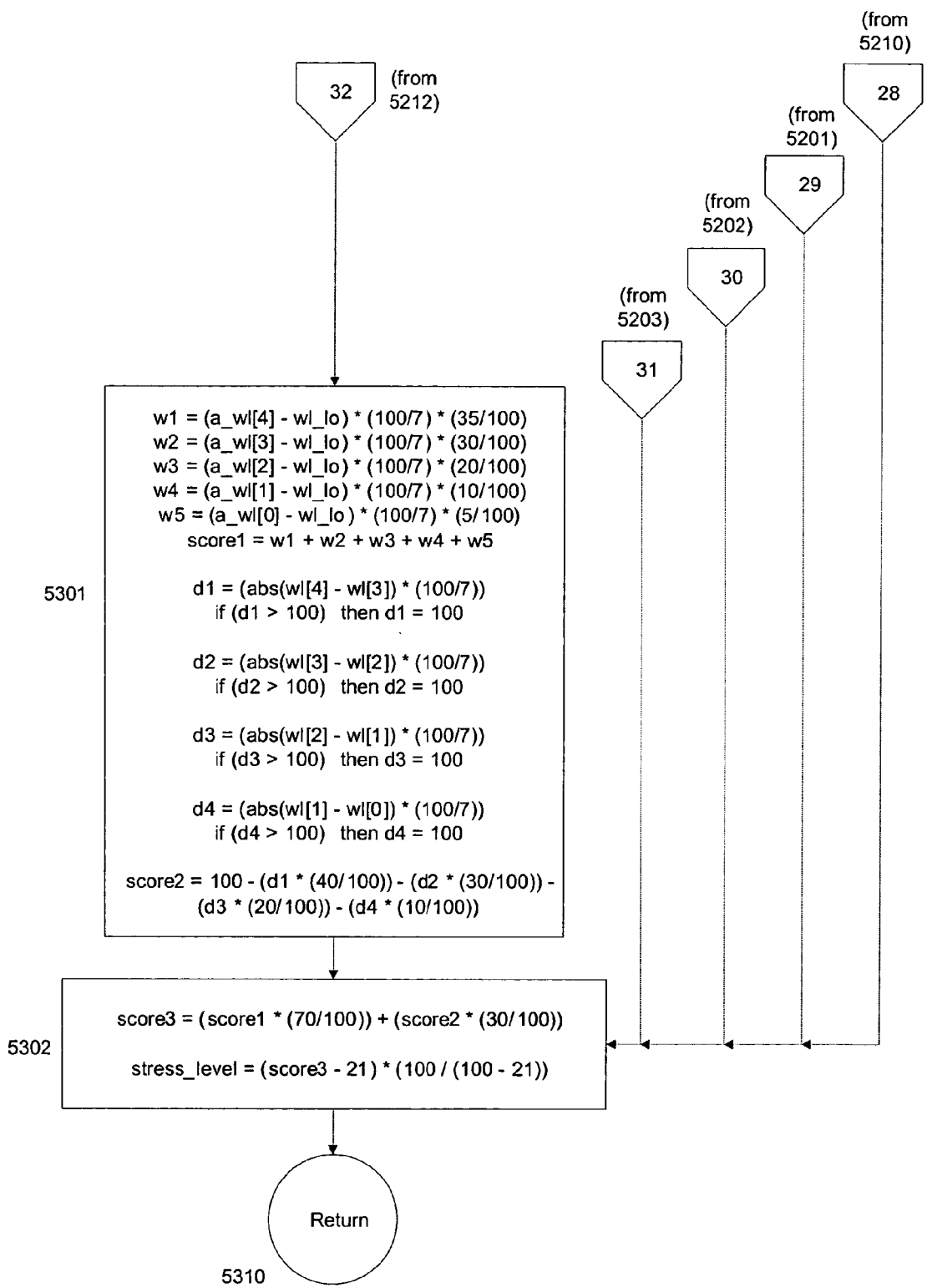

FIGS. 38-42 depict process flow of an exemplary main routine according to an exemplary embodiment of the present invention, entitled Process Pulse. Process Pulse calls the subroutines error_correction (FIGS. 43-45), error detection (FIGS. 46-47), initialize_range (FIG. 48) and process_waves (FIGS. 49-50). In turn, process_waves calls subroutines get_waves (FIGS. 8(a)-(b)) and determine_stress (FIGS. 51-53). Thus all of the subroutines are called, directly or indirectly, by Process Pulse.

Figure 38:
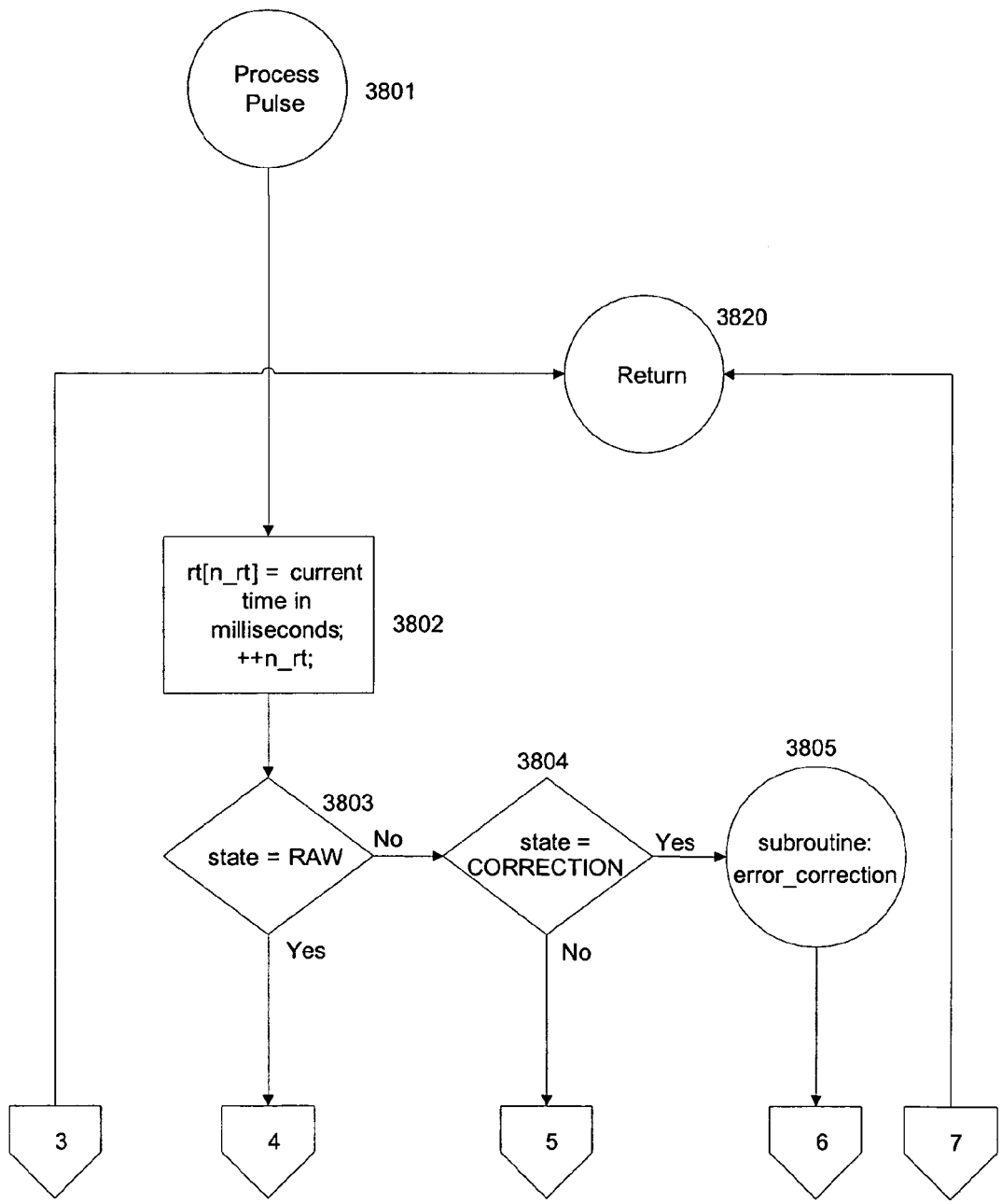
FIGS. 38-42 depict an exemplary process flow for an exemplary procedure for processing a detected pulse according to an exemplary embodiment of the present invention.
Figure 39:
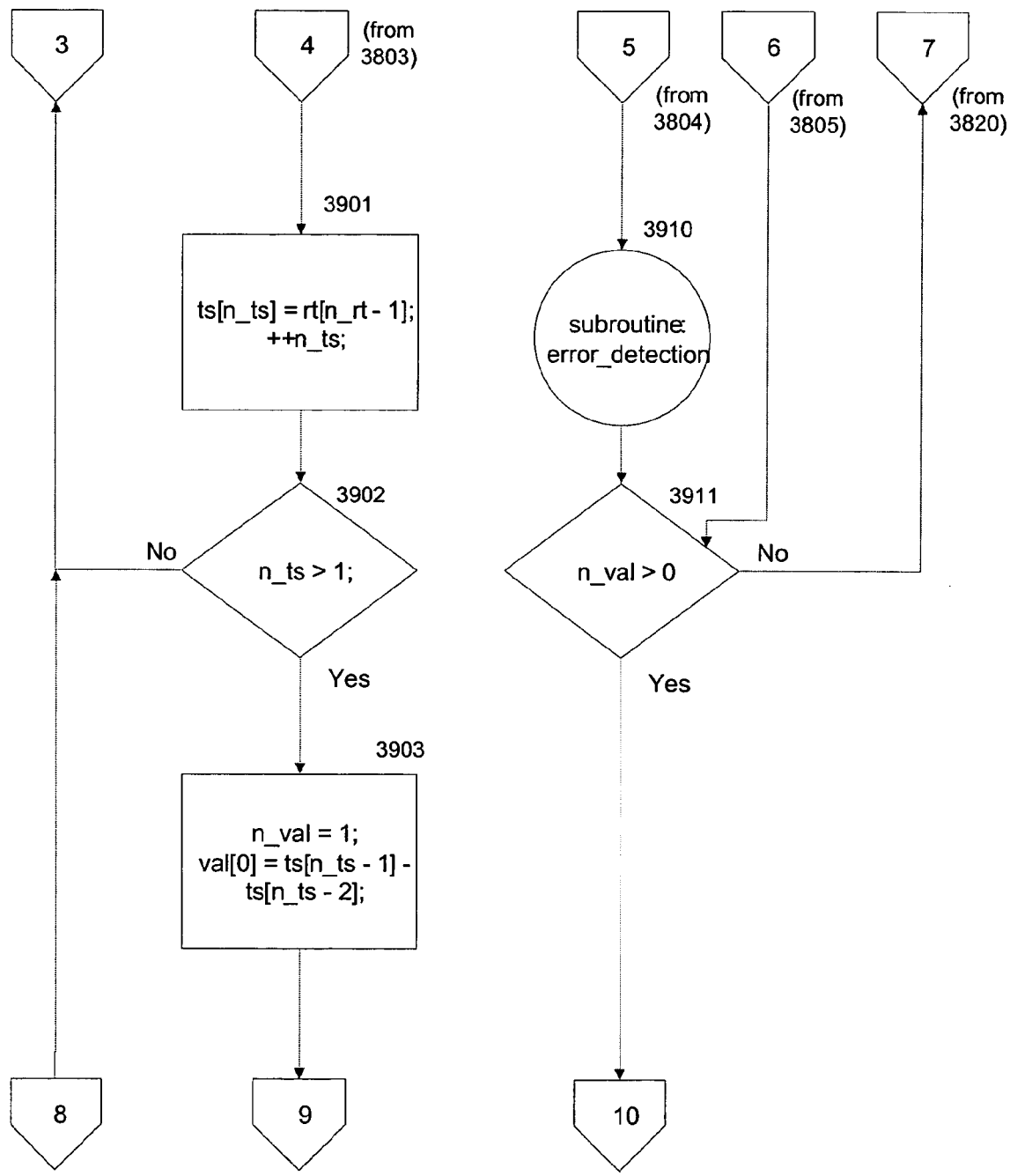

With reference to FIG. 38, at 3802, the raw timestep rt[n_rt], which is rt[0], given the initialization at 3601 of FIG. 36, is set to the current time in milliseconds, and nrt, or the number of raw timesteps, is preincremented. Then, for example, at 3803, 3804 and 3805, the variable state can be tested for being RAW, DETECTION or CORRECTION to determine whether the data is assumed to be error-free, suspect or erroneous, and accordingly along which path process flow will continue. If state=CORRECTION the data path beginning at 3805 will be taken, calling an error correction subroutine at 3805. If state=DETECTION, the data path beginning at 3804 will be taken, ultimately calling an error detection subroutine at 3910 of FIG. 39. These two data pathways ultimately arrive at 4011 of FIG. 40. If state=RAW, process flow can continue directly to 3901 of FIG. 39 where timing variables are initialized, including preincrementing n_ts, a variable that tracks the number of timesteps, and through 3902 where n_ts is verified to be greater than one. If that is the case, at 3903, for example, n_val, the number of pp intervals to be assigned, can, for example, be set equal to 1, and process flow can continue, through breakpoint 9, to 4010 of FIG. 40, and through to 4011. When process flow reaches 4011 there are one or more pp values needing to be assigned. Thus, at 4011, each pp value is assigned a value and if there are more than one pp values (i.e., n_val>1) then the actual time steps can be generated, and the instantaneous pulse rate is displayed, which is the frequency of the current pp interval determined by (60000/pp[n_pp-1]). From 4011 process flow continues to 4110, where if there are more than one pp values, calculation of interbeat intervals (IBI's) is possible. This at 4110 the process tests for this condition, and if yes, IBI values can, for example, be calculated at 4111. If not, process flow can loop back to 4010. At 4111, once IBI values are calculated, process flow moves to 4201 to test how many pp values there are. If there are more than 8, i.e., at least 9, then there is sufficient data to identify a level 4 valley. Once there is are at least two level 4 valley points, i.e., num_val4>1 at 4212 the exemplary process can look for RSA waves, as described above. Thus, a yes at 4212 can, for example, cause the process flow to call a process_waves subroutine at 4213.

Figure 43:
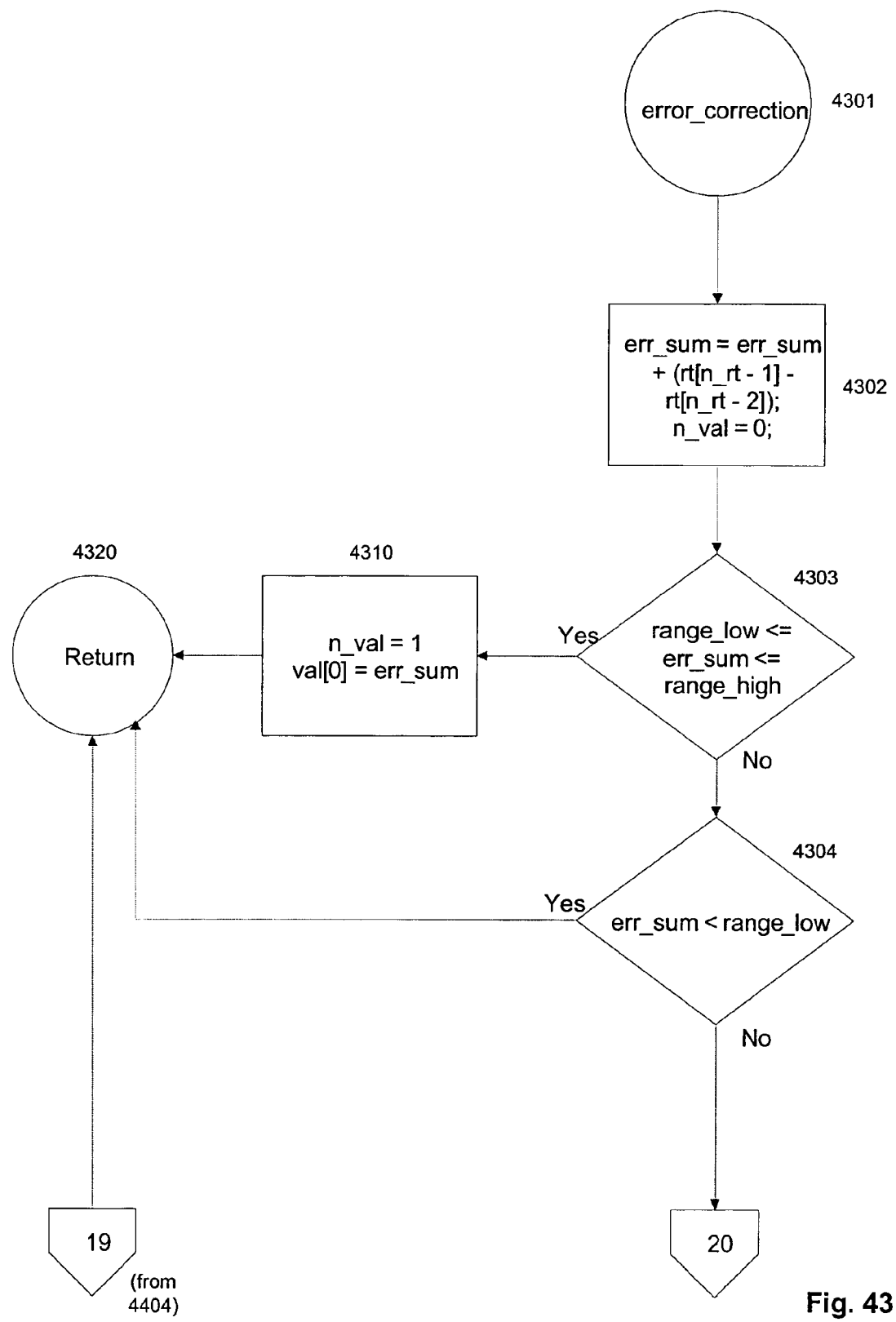
FIGS. 43-45 depict an exemplary process flow for an exemplary procedure for error correction for a sequence of detected pulses according to an exemplary embodiment of the present invention.
Figure 44:
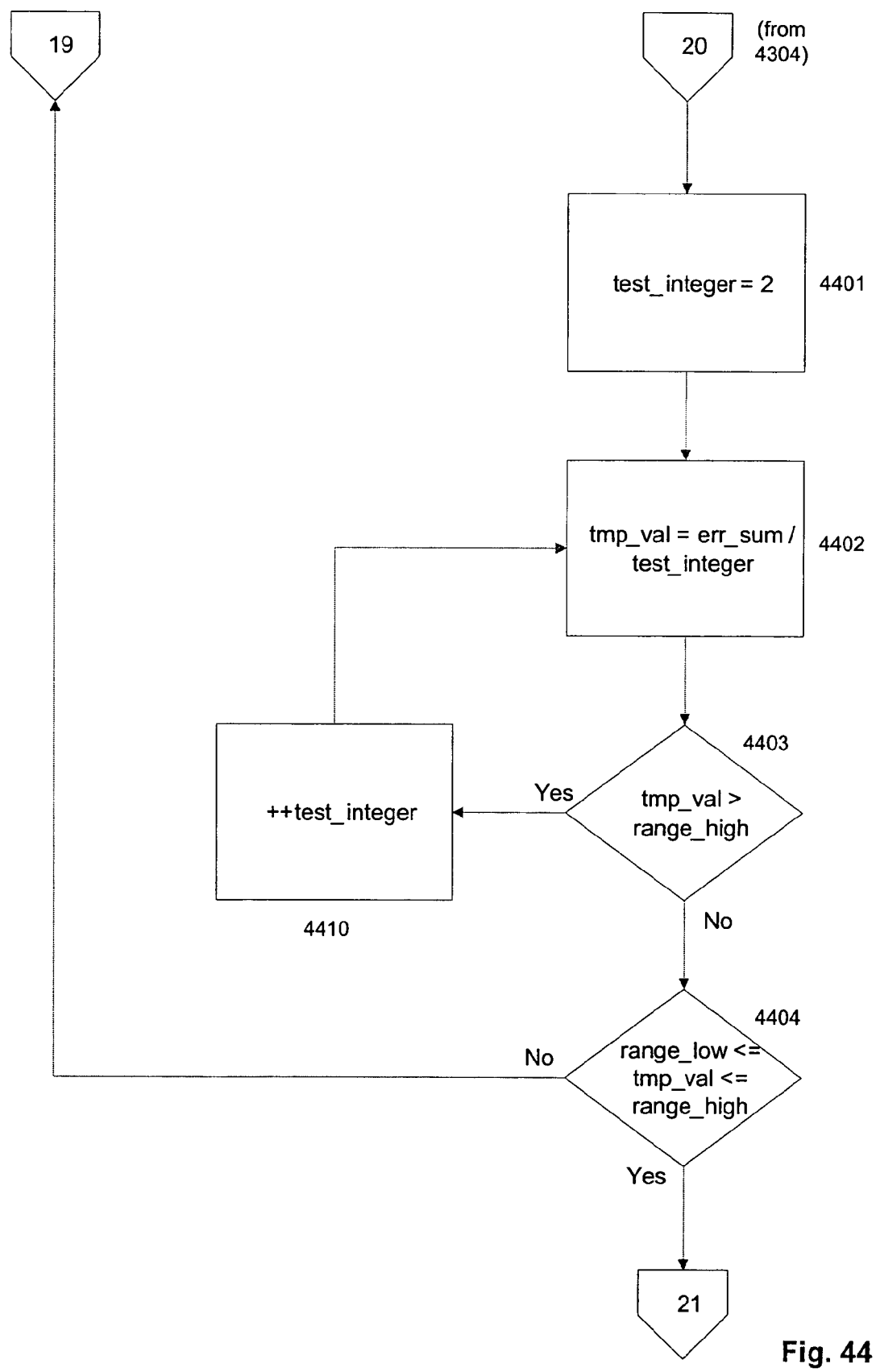
Figure 45:
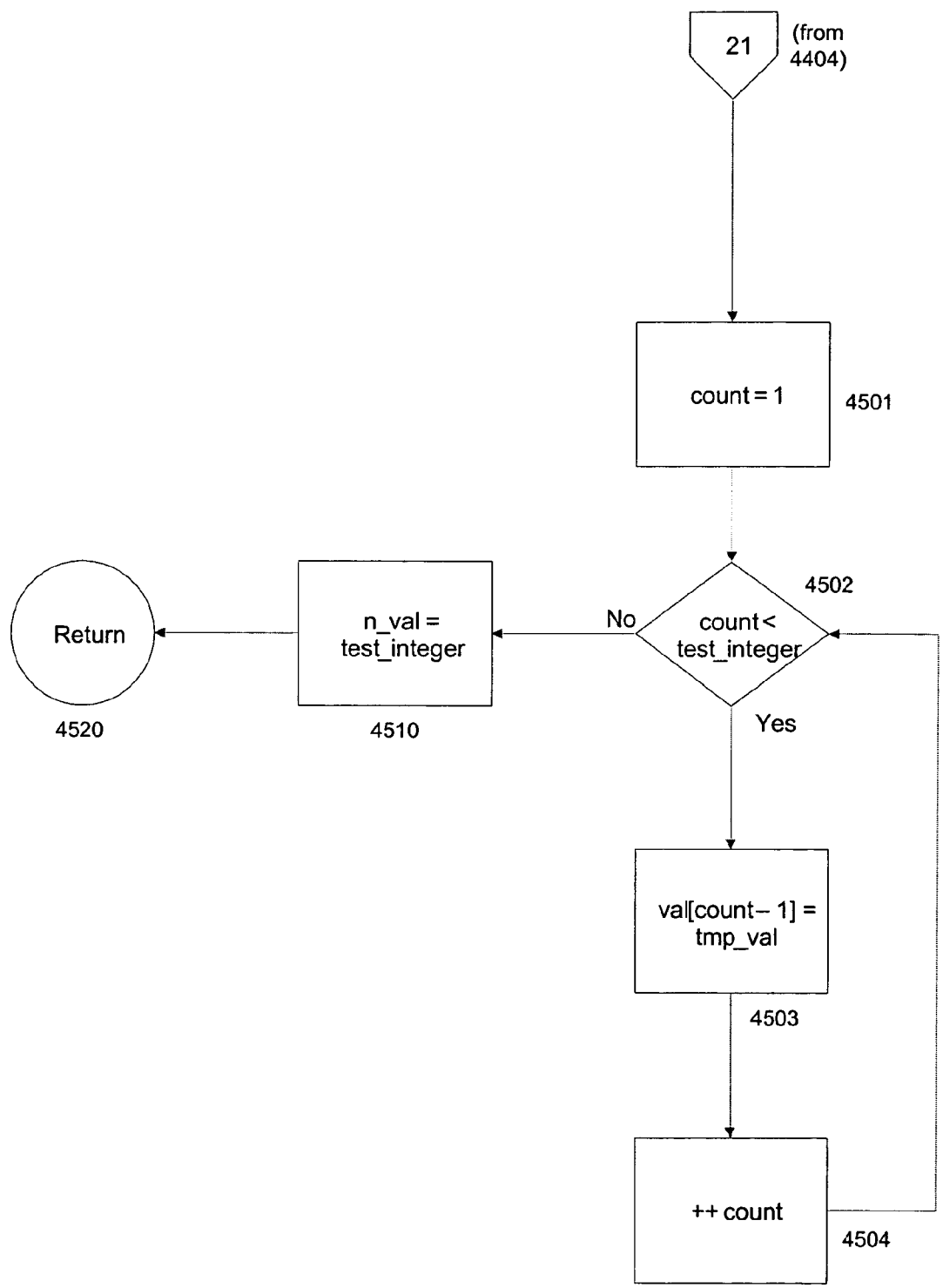

FIGS. 43-45 depict an exemplary process flow for an error correction subroutine. As described above in connection with the exemplary Process Pulse routine, at 3805 of FIG. 38, an error correction subroutine is called. With reference to FIG. 43, process flow begins at 4301, where the subroutine begins. At 4302, for example a variable err_sum, which accumulates current pp interval times, has the most recent pp interval added to it. Additionally, the variable n_val is set to 0. Process flow continues at 4303, where the new value for err_sum is tested as to whether it is in range. If it is in range, process flow can move, for example, to 4310, where the variable n_val is set to 1, representing a correct pp interval being identified, and the value of that pp interval is set equal to the number of milliseconds in err_sum, and process flow returns at 4320 to Process Pulse. On the other hand, if at 4303 the tentative pp interval time is not within range, process flow can move to 4304, where, for example, the subroutine tests whether the current pp interval time is below the range. If yes, process flow returns to 4302 and an additional pp interval time is added to the variable err_sum. If no, then the current sum is considered as too high and a suitable integer must be found with which to divide it to create two or more "in range" pp intervals. Process flow then continues from 4304 through breakpoint 20 to 4401 of FIG. 44.

There, test_integer=2 is set as a test divisor and process flow can move, for example, to 4402 where a temporary variable tmp_val is set up to hold the quotient of err_sum/test_integer, representing a possible actual corrected pp interval. Process flow can then move to 4403, where, for example, tmp_val is tested for being above the range. If yes, then at 4410, for example, the test_integer variable is incremented and the proposed division occurs one more time at 4402. On the other hand, if at 4403 tmp_val is not above the range, than at 4404, for example, tmp_val can again be tested for being within the range, and if yes, process flow can move (through breakpoint 21) to 4501 of FIG. 45.

At 4501 of FIG. 45, a count variable can be set to 1, and at 4502, for example, the subroutine can query whether count is less than the current value of test_integer. If no, then process flow can move, for example, to 4510, and the variable n_val can be set equal to test_integer and at 4520, for example, return to Process Pulse, at breakpoint 6 of FIG. 38. On the other hand, if count is less than test_integer at 4502, then process flow can, for example, loop through 4503, 4504 and 4502, incrementing the value of count each loop (at 4504) until count equals test_integer, at which time process flow can return to Process Pulse.

Figure 46:
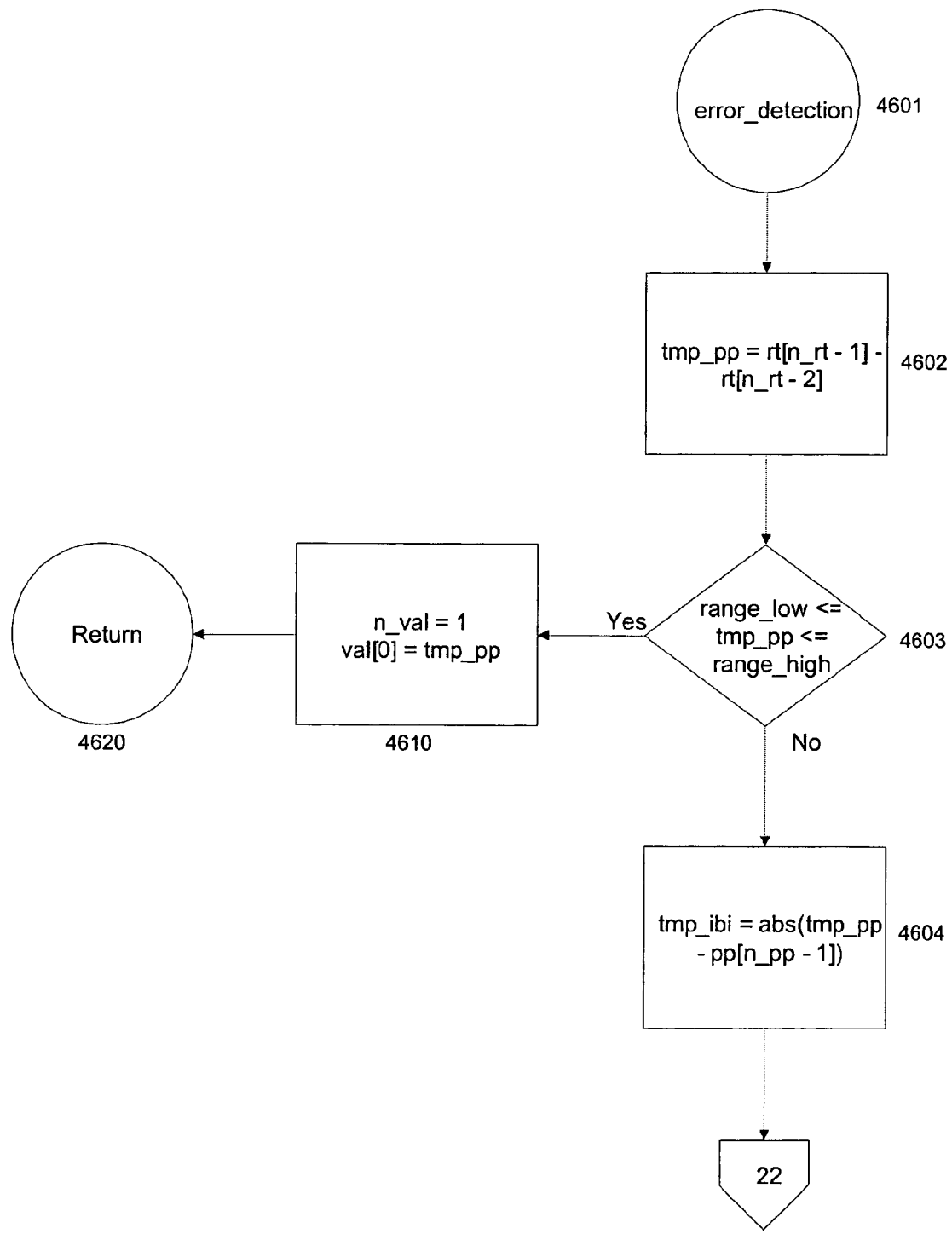
FIGS. 46-47 depict an exemplary process flow for an exemplary procedure for error detection for a sequence of detected pulses according to an exemplary embodiment of the present invention.
Figure 47:
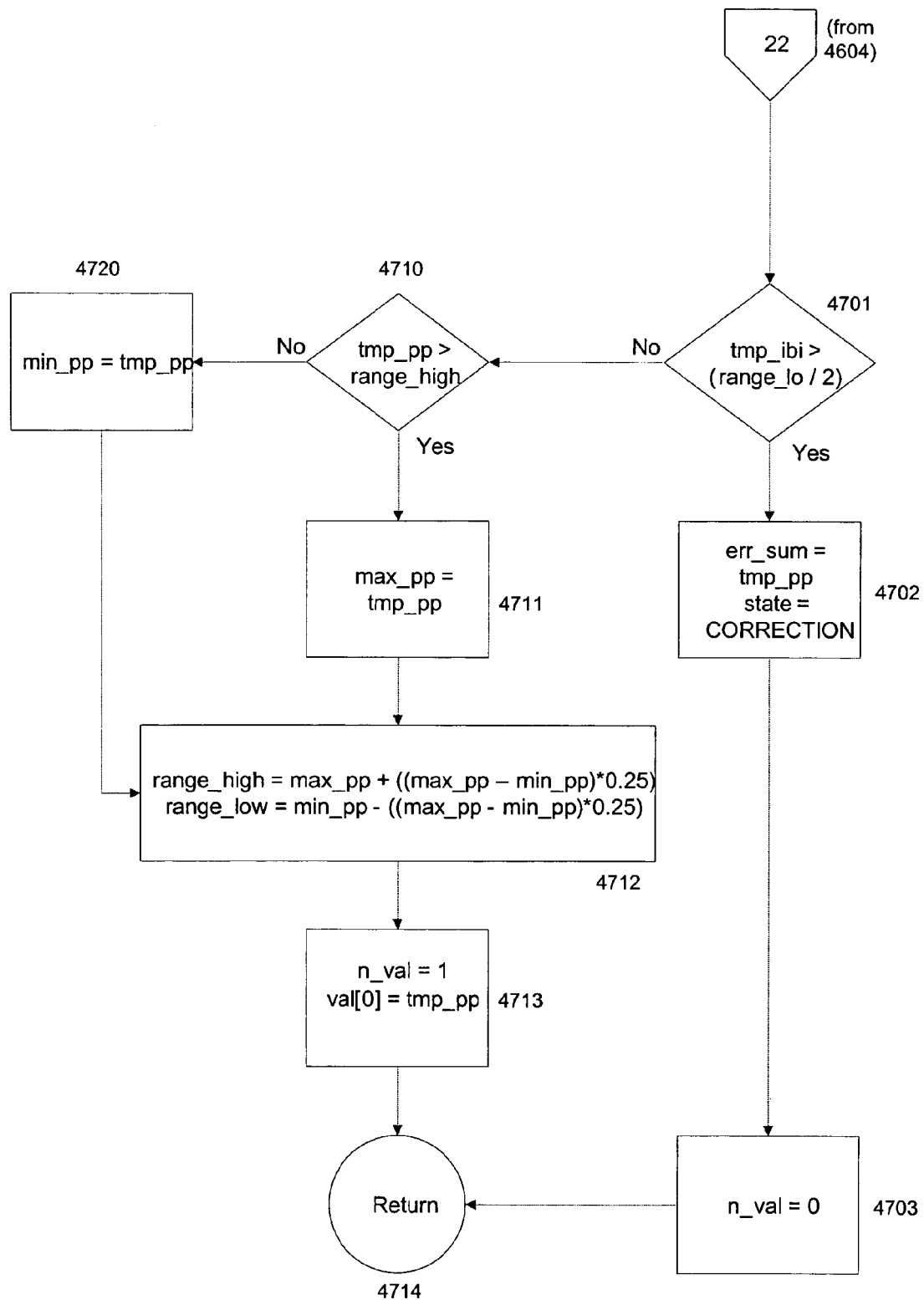

Next described is an exemplary error detection subroutine with reference to FIGS. 46-47. With reference to FIG. 46, process flow begins at 4601 and continues to 4602, where a current pp interval is loaded into temporary (in the sense of tentatively correct) pp interval tmp_pp. At 4603, the tmp_pp is tested for being within range. If yes, then n_val is set to 1 and val[0] is set equal to tmp_pp at 4610 and at 4620 process flow returns to the calling program, Process Pulse, in particular to 3911 in FIG. 39. However, if at 4603 tmp_pp is found to be out of range then, at 4604, temporary interbeat interval variable tmp_ibi is generated to use in detecting any errors as described above. Process flow can then continue (through breakpoint 22) to 4701 of FIG. 47, where tmp_ibi is tested for being greater than half the lower end of the range, which is a test for being too large, as described above. If yes, there is assumed to be an error, and flow continues to 4702, where the variable err_sum is set equal to tmp_pp (err_sum is an input to the error correction subroutine described above), "state" is set to be CORRECTION, and process flow can move, for example, to 4703 where n_val is set to 0 and process flow returns to Process Pulse, which can then, based on n_val=0 and state=CORRECTION, return at 3911 of FIG. 39 to 3820 of FIG. 38, and ultimately flow to an error-correction subroutine at 3805.

If at 4701 tmp_ibi is not greater than half of the lower end of the range, in which case it is not considered to be large and thus no error present in the pp interval data, process flow can continue to 4710, and, for example, test whether the tmp_pp is greater than the top of the range. Because tmp_ibi was not found to be large at 4701, and thus no error is assumed present, if at 4710 the tmp_pp interval is still larger than the existing top of the range, the range needs to be recalculated using the new pp interval as max_pp, which holds the value for the maximum possible pp interval which is not the result of an error in the data. At 4711, for example, max_pp can be set equal to tmp_pp and, using this new value, at 4712, for example, the upper and lower ends of the range are recalculated. Flow can then continue, for example, to 4713 where the n_val is set equal to 1 and val[0] is set equal to the current pp interval, tmp_pp. At 4714, for example, process flow can return to the calling routine Process Pulse. If at 4710 the current pp interval is not greater than the existing upper end of the range then, for example, at 4720 the minimum possible pp interval is set equal to the current pp interval. Then process flow continues as described above through 4712, 4713 and 4714, where process flow returns to the calling program.

Figure 48:
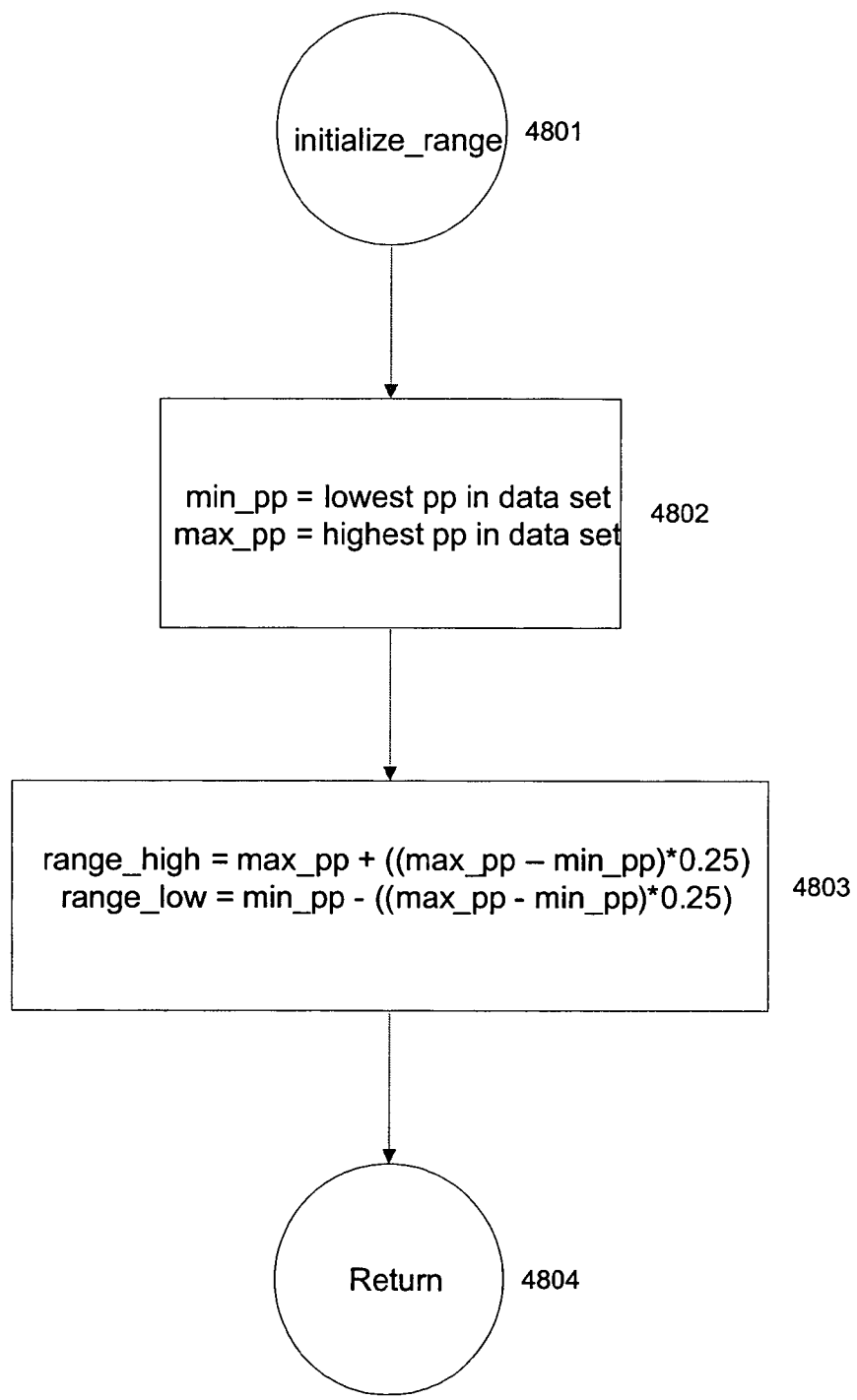
FIG. 48 depicts an exemplary process flow for an exemplary procedure for initializing a range for detected pulses according to an exemplary embodiment of the present invention.

With reference to FIG. 48, process flow for the subroutine initialize_range is next described. This subroutine can be used in exemplary embodiments of the present invention to calculate the range for pp intervals within which the data is assumed to be error free, for use in the error detection and correction routines. Beginning at 4801 at the subroutine call, process flow moves, for example, to 4802, where the variables min_pp and max_pp are set using the following pseudocode: min_pp=lowest pp in data set; max_pp=highest pp in data set. Then, for example, at 4803, the upper and lower ends of the range of data points used for error detection and correction, as described above. This can, for example, be implemented using the following pseudocode: range_high=max_pp+((max_pp−min_pp)*0.25); range_low=min_pp−((max_pp−min_pp)*0.25). Using these exemplary values, the range is now set, and at 4804 process flow returns to the calling routine, i.e., Process Pulse. In particular, process flow returns to 4102 in FIG. 41.

FIGS. 49-50 depict an exemplary process flow for a wave processing subroutine. In an exemplary embodiment of the present invention, such a subroutine can be called, for example, by a pulse acquisition processing routine such as Process Pulse, as described above. After the subroutine is called at 4901, for example, process flow can continue at 4902, where the get_waves subroutine described above can be called to input the waves identified from the pulse data. Process flow continues, for example, to 4903, where, given the acquired waves, a score indicative of a user's stress level reflected in the identified waves can be assigned using an exemplary determine_stress subroutine. Flow can then continue, for example, to 4904 where the waves are sorted and the instantaneous frequency calculated based on the current pp interval using the expression frequency=60000/(ppts[v2[n_waves-1]]−ppts[v1[n_waves-1]]), where ppts[v] is the pulse point time stamp at data point v. From there, for example, process flow can continue to 5001 on FIG. 50, where a score between 0-3 can be assigned to a user based upon the frequency of the current wave, where a higher score indicates a lower stress level. At 5002, for example, the subroutine can, for example, display to the user each of his or her (i) stress level (obtained from the call to determine_tress at 4903); (ii) frequency (from 4904); and (iii) score (from 5001), at which point, for example, at 5003, process flow can return to the calling routine, Process Pulse.

FIGS. 51-53 depict an exemplary subroutine for determining a stress score. What is being measured is how unrelaxed a given user is, by operating on the wavelengths of his or her RSA waves. With reference to FIG. 51, at 5104 the determine_stress subroutine calls assigned_wavelengths, which assigns a wavelength between wl_lo and wl_high (which are set at 5102) to each wave. Using these wavelengths and how many waves there are (i.e., the value of n_waves), FIGS. 51-52 depicts process flow for each value of n_waves between 1 and 4. A score1 is determined at each of 5110, 5201, 5202 and 5203, which is a weighted sum of the differences between each wave's wavelength and w_lo, which measures how far off the baseline that particular wave is. Thus, a perfect relaxation score would have a_w[n]=w_lo for all n, and each score1 would equal zero. In alternate exemplary embodiments of the present invention score1 can be calculated without weighting the sums of differences, and this is the method as described above. Score1 is what was described as the "wavelength" score. As can be seen at each of 5110, 5201, 5202 and 5203, a "variance" score, score2 is also computed. Score1 and score2 can be combined at 5302 using a 70/30 relative contribution factor to obtain score3. Other relative weightings can be used in alternate exemplary embodiments according to the present invention as may be found useful. Score3 can be used to calculate stress_level using, for example, the equation stress_level=(score3−21)*(100/(100−21)). Stress_level is returned to process_waves at 4903.

Figure 54:
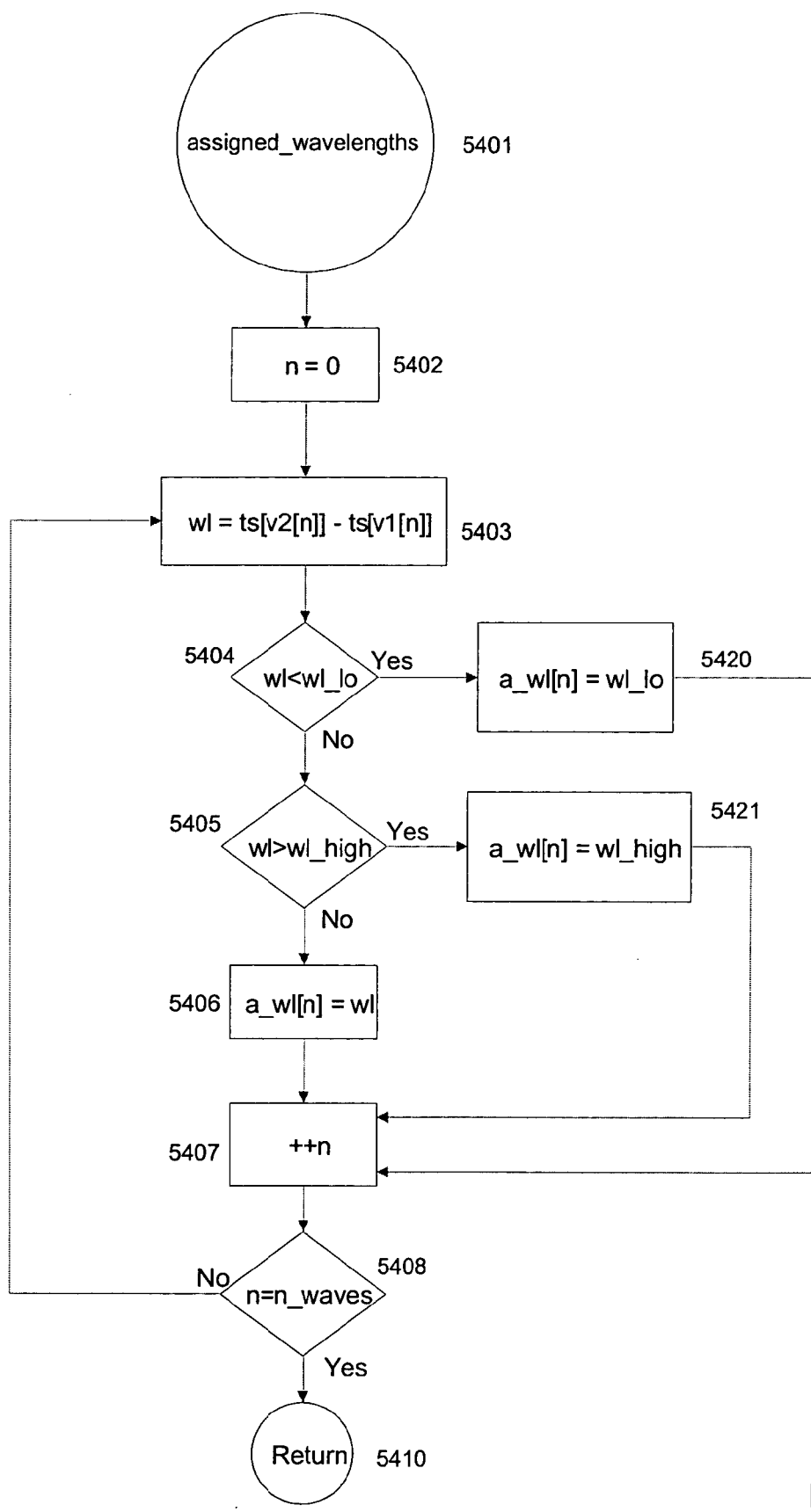
FIG. 54 depicts an exemplary process flow for an exemplary procedure for assigning wavelengths to RSA waves according to an exemplary embodiment of the present invention.

With reference to FIG. 54, an exemplary subroutine for assigning wavelengths to acquired waves is depicted. This subroutine can be used, for example, in the exemplary determine_stress routine depicted in FIGS. 51-53, as described above, which takes wavelengths as inputs. In an exemplary embodiment of the present invention, process flow can begin at 5401 with a call to the subroutine. At 5402 a counter variable n is set equal to zero, and at 5403, for example, a current wavelength wl is calculated by subtracting the timestamp of the current v2 from that of the current v1, using the expression wl=ts[v2[n]]−ts[v1[n]]. At 5404 and 5405, for example, the value of wl is compared with that of wl_lo and wl_high, which can be set in the calling subroutine as seen at 5102 of FIG. 51 (where, for example, they are set as 3 and 10, respectively). If wl is less than wl_lo or higher than wl_high, a_wl[n] is truncated at either wl_lo or wl_high, as the case may be, and flow continues at 5407 where the value of n is preincremented. If, however, wl has a value between wl_low and wl_high, then, for example, at 5406, a_wl[n] is set to wl, and process flow continues to 5407. At 5408 the value of n is compared with that of n_waves, to insure that each acquired wave has been assigned a wavelength. If they are equal, at 5410, for example, process flow ends for this subroutine, and returns to 5105 in FIG. 51. If they are not equal, then flow loops through 5403 for each acquired wave until all acquired waves have been assigned wavelengths.

The invention claimed is:

1. A handheld portable biofeedback device for reducing stress in a human subject comprising:
   a housing:
   a photoplethysmograph sensor disposed in the housing, wherein the photoplethysmograph sensor generates data from the human subject;
   a control system coupled to the photoplethysmograph sensor; and
   display screen,
   wherein the control system is configured to process the data from the human subject for output to the display screen, the output data providing the human subject with information associated with the human subject's stress level; and
   wherein the housing, photoplethysmograph sensor, control system and display screen form an integrated structure,
   wherein during respiration of the human subject said device is configured to record multiple heart rate related intervals of the human subject; and
   analyze a portion of the multiple heart rate related intervals sufficient to delineate at least one individual respiratory sinus arrhythmia wave, and
   wherein the control system is further configured to determine a first value indicative of the human subject's stress level by determining how far average wavelengths of the respiratory sinus arrhythmia wave deviate from a level that represents a relaxed state of the user.

2. The device of claim 1, wherein a heart rate related interval of the multiple heart rate related intervals is a pulse peak interval.

3. The device of claim 1, wherein a heart rate related interval of the multiple heart rate related intervals is a R wave interval.

4. The device of claim 1, wherein said delineation includes identifying a set of transition points in each individual respiratory sinus arrhythmia wave.

5. The device of claim 4, wherein the set of transition points includes at least one top point and at least two bottom points.

6. The device of claim 1, further comprising a breathing metronome configured to being activated by the human subject, wherein the breathing metronome is programmed to deactivate after a predetermined period of time.

7. The device of claim 1, wherein the device configured to extract information related to respiration of the human subject.

8. The device of claim 7, wherein the information related to respiration includes rate, rhythm and volume.

9. The device of claim 1, wherein the control system is further configured to compute a second value indicative of how irregular the respiratory sinus arrhythmia wave occurs, and to combine the first value and the second value to form an overall value indicative of an overall stress level the human subject.

* * * * *